United States Patent
Sudo et al.

(10) Patent No.: US 10,849,569 B2
(45) Date of Patent: Dec. 1, 2020

(54) BIOLOGICAL INFORMATION MEASUREMENT DEVICE AND SYSTEM

(71) Applicant: KABUSHIKI KAISHA TOSHIBA, Minato-ku (JP)

(72) Inventors: Takashi Sudo, Fuchu (JP); Takaya Matsuno, Kunitachi (JP); Masataka Osada, Kawasaki (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 689 days.

(21) Appl. No.: 15/444,620

(22) Filed: Feb. 28, 2017

(65) Prior Publication Data

US 2017/0172521 A1    Jun. 22, 2017

Related U.S. Application Data

(63) Continuation of application No. PCT/JP2015/076103, filed on Sep. 15, 2015.

(30) Foreign Application Priority Data

Sep. 22, 2014  (JP) .................................. 2014-192209
Sep. 22, 2014  (JP) .................................. 2014-192750

(51) Int. Cl.
*A61B 5/00*  (2006.01)
*A61B 5/026*  (2006.01)
(Continued)

(52) U.S. Cl.
CPC .......... *A61B 5/7285* (2013.01); *A61B 5/0205* (2013.01); *A61B 5/0261* (2013.01);
(Continued)

(58) Field of Classification Search
CPC ... A61B 5/7285; A61B 5/7264; A61B 5/0261; A61B 5/4812; A61B 7/04; A61B 7/003;
(Continued)

(56) References Cited

U.S. PATENT DOCUMENTS 5,941,837 A    8/1999   Amano et al.
8,521,681 B2   8/2013   Ouchi et al.
(Continued)

FOREIGN PATENT DOCUMENTS

JP    2004-121864 A    4/2004
JP    2006-263054 A    10/2006
(Continued)

OTHER PUBLICATIONS

International Search Report dated Dec. 15, 2015, in PCT/JP2015/076103, filed Sep. 15, 2015.

*Primary Examiner* — Eric F Winakur
*Assistant Examiner* — Abid A Mustansir
(74) *Attorney, Agent, or Firm* — Oblon, McClelland, Maier & Neustadt, L.L.P.

(57) ABSTRACT

According to one embodiment, a biological information measurement device includes: a biological information measurer configured to carry out intermittent measurement of biological information of a user; a motion information measurer configured to measure motion information of the user; a feature calculator configured to calculate a feature from the motion information; a behavior state determiner configured to determine a behavior state of the user on the basis of the feature; and a measurement interval controller configured to select one intermittent measurement from a plurality of intermittent measurements having different measurement intervals on the basis of the determined behavior state of the user and control the biological information measurer.

4 Claims, 24 Drawing Sheets

(51) Int. Cl.
*A61B 5/0205* (2006.01)
*A61B 5/11* (2006.01)
*A61B 5/1455* (2006.01)
*A61B 5/16* (2006.01)
*A61B 7/00* (2006.01)
*A61B 7/04* (2006.01)
*A61B 5/024* (2006.01)

(52) U.S. Cl.
CPC ........ *A61B 5/1118* (2013.01); *A61B 5/14552* (2013.01); *A61B 5/165* (2013.01); *A61B 5/4803* (2013.01); *A61B 5/4809* (2013.01); *A61B 5/4812* (2013.01); *A61B 5/4818* (2013.01); *A61B 5/6831* (2013.01); *A61B 5/6843* (2013.01); *A61B 5/7264* (2013.01); *A61B 7/003* (2013.01); *A61B 7/04* (2013.01); *A61B 5/0022* (2013.01); *A61B 5/02427* (2013.01); *A61B 5/1123* (2013.01); *A61B 5/6824* (2013.01); *A61B 5/6826* (2013.01); *A61B 2562/0204* (2013.01); *A61B 2562/0219* (2013.01)

(58) Field of Classification Search
CPC ... A61B 5/6843; A61B 5/6831; A61B 5/4818; A61B 5/4809; A61B 5/4803; A61B 5/165; A61B 5/14552; A61B 5/1118; A61B 5/0205; A61B 5/1123; A61B 5/6826; A61B 2562/0219; A61B 2562/0204; A61B 5/6824; A61B 5/0022; A61B 5/02427
See application file for complete search history.

(56) References Cited

U.S. PATENT DOCUMENTS

| | | | |
|---|---|---|---|
| 2003/0055654 A1* | 3/2003 | Oudeyer | G10L 13/033 704/275 |
| 2006/0217603 A1 | 9/2006 | Nagai et al. | |
| 2007/0276669 A1* | 11/2007 | Humble | G10L 17/26 704/270 |
| 2008/0308105 A1* | 12/2008 | Alder | A61B 5/097 128/204.23 |
| 2009/0227888 A1* | 9/2009 | Salmi | A61B 5/1118 600/534 |
| 2010/0217588 A1 | 8/2010 | Ouchi et al. | |
| 2013/0179110 A1* | 7/2013 | Lee | A61B 5/1118 702/130 |
| 2016/0220198 A1* | 8/2016 | Proud | A61B 5/4809 |

FOREIGN PATENT DOCUMENTS

| | | |
|---|---|---|
| JP | 2007-330708 A | 12/2007 |
| JP | 2008-43356 A | 2/2008 |
| JP | 2010-190861 A | 9/2010 |
| JP | 2011-193886 A | 10/2011 |
| JP | 2013-22360 A | 2/2013 |
| JP | 2013-150660 A | 6/2013 |
| JP | 2016-59736 A | 4/2016 |
| JP | 2016-59765 A | 4/2016 |

* cited by examiner

| TIME | SLEEPING/WAKING | SpO$_2$ VALUE | REFERENCE SpO$_2$ | REFERENCE VALUE GRAPH |
|---|---|---|---|---|
| 0:00 | WAKING | 98 | 98 | ○ |
| 0:20 | WAKING | 97 | 98 | |
| 0:30 | SHALLOW SLEEP | 97 | 97 | ○ |
| 0:35 | DEEP SLEEP | 95 | 97 | |
| 0:40 | DEEP SLEEP | 87 | 97 | |

BIOLOGICAL INFORMATION MEASUREMENT DEVICE AND SYSTEM

CROSS REFERENCE TO RELATED APPLICATIONS

This application is a Continuation of International Application No. PCT/JP2015/076103, filed on Sep. 15, 2015, the entire contents of which is hereby incorporated by reference.

FIELD

Embodiments described herein relate to a biological information measurement device and a biological information measurement system.

BACKGROUND

Conventionally, in medical institutions and other relevant entities, measurement of arterial oxygen saturation ($SpO_2$) has been performed to discover sleep apnea syndrome (SAS), respiratory failure (asthma, etc.), and the like. In the trend in recent years of downsizing of a measurement device (pulse oxymeter) that measures $SpO_2$, there have been increasing needs for personal, daily, constant use of the measurement device.

In order to meet the needs, wearable devices that are capable of measuring $SpO_2$ such as a ring-type device have been proposed.

DETAILED DESCRIPTION

According to one embodiment, a biological information measurement device includes: a biological information measurer configured to carry out intermittent measurement of biological information of a user; a motion information measurer configured to measure motion information of the user; a feature calculator configured to calculate a feature from the motion information; a behavior state determiner configured to determine a behavior state of the user on the basis of the feature; and a measurement interval controller configured to select one intermittent measurement from a plurality of intermittent measurements having different measurement intervals on the basis of the determined behavior state of the user and control the biological information measurer.

Embodiments of the present invention will be described below with reference to the drawings.

First Embodiment

A biological information measurement device (hereinafter referred to as "measurement device") and a biological information measurement program (hereinafter referred to as "measurement program") in accordance with a first embodiment are described with reference to FIGS. 1 to 6.

Figure 1:
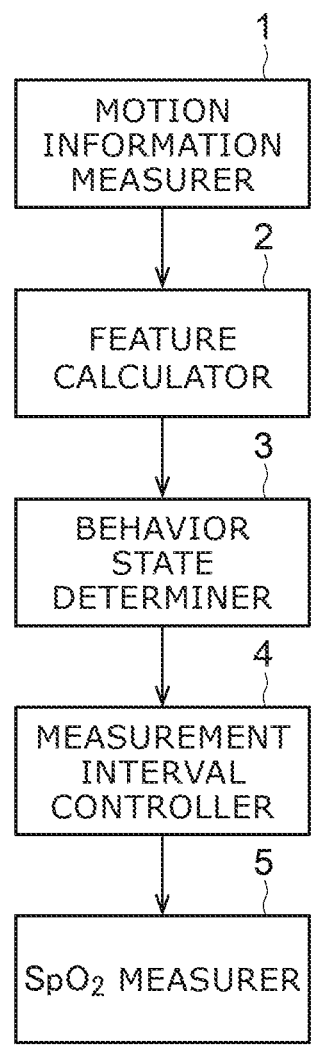
FIG. 1 is a schematic diagram illustrating a functional configuration of a biological information measurement device in accordance with a first embodiment.

First, a functional configuration of the measurement device in accordance with this embodiment is described with reference to FIG. 1. FIG. 1 is a schematic diagram that illustrates the functional configuration of the measurement device in accordance with this embodiment. As illustrated in FIG. 1, the measurement device includes a motion information measurer 1, a feature calculator 2, a behavior state determiner 3, a measurement interval controller 4, and an $SpO_2$ measurer 5.

The motion information measurer 1 is configured to measure motion information indicative of a motion of a user. The motion information represents, by way of example and is not limited to, acceleration and angular velocity. The motion information measurer 1 includes a motion information sensor adapted to detect the motion information such as an acceleration sensor and an angular velocity sensor (gyro sensor), and calculates the motion information from an output signal that is output from the motion information sensor. The motion information measurer 1 operates continuously or intermittently at time intervals of not more than 10 seconds while the measurement device is operating, and measures the motion information. Also, it should be noted that one or more pieces of motion information may be measured by the motion information measurer 1.

The feature calculator 2 is configured to calculate one or more features from the motion information measured by the motion information measurer 1. The feature is, by way of example and not limited to, an amount of motion of a body (which is hereinafter referred to as "body motion amount").

The behavior state determiner 3 is configured to determine a behavior state of the user on the basis of the feature calculated by the feature calculator 2. The behavior state determined by the behavior state determiner 2 includes, by way of example and is not limited to, sleeping, waking, complete standstill (measurement device not being attached), walking, running, riding on a train, car, or bus, bicycling, being aboard an airplane, being aboard a ship, swimming, playing tennis, taking part in an individual sport, taking part in a team sport, dining, drinking and eating, doing desk work, lying in a supine position, and being seated.

The measurement interval controller 4 is configured to select one intermittent measurement from among multiple intermittent measurements having different measurement intervals on the basis of the behavior state of the user determined by the behavior state determiner 3, and control the measurement interval of $SpO_2$ by the $SpO_2$ measurer 5. The method of controlling the measurement interval will be described later.

The $SpO_2$ measurer 5 (biological information measurer) is configured to intermittently measure (or carry out intermittent measurement of) $SpO_2$ of the user at predetermined time intervals. The measurement interval of the $SpO_2$ measurer 5 is, as described above, controlled by the measurement interval controller 4. The $SpO_2$ measurer 5 includes an $SpO_2$ sensor and calculates $SpO_2$ from the output signal of the $SpO_2$ sensor.

The $SpO_2$ sensor includes an R light source adapted to emit a red light (R light), an IR light source adapted to emit an infrared light (IR light), and a light reception section. The R light source and the IR light source are, by way of example, LEDs, which irradiate the measurement site of $SpO_2$ (an arm, a finger, etc. of the user) with the R light and the IR light, respectively. The light reception section is, by way of example, a photoelectric element adapted to receive the light transmitted through or reflected by the measurement site and output a signal in accordance with the intensity of the received light.

Hemoglobin to which oxygen is bound ($HbO_2$) and hemoglobin to which oxygen is not bound (Hb) have different absorbance values with respect to the R light and the IR light. As a consequence, the $SpO_2$ measurer 5 is allowed to calculate $SpO_2$ by obtaining a ratio between the extinction degrees of the R light and the IR light from the output signal that is output from the light reception section.

Next, the hardware configuration of the measurement device in accordance with this embodiment is described with reference to FIG. 2. The measurement device in accordance with this embodiment includes a computer device 100. The output signals that are output from the motion information sensor, the $SpO_2$ sensor, and the like are input to the computer device 100 and subjected to a predetermined process or processes.

Figure 2:
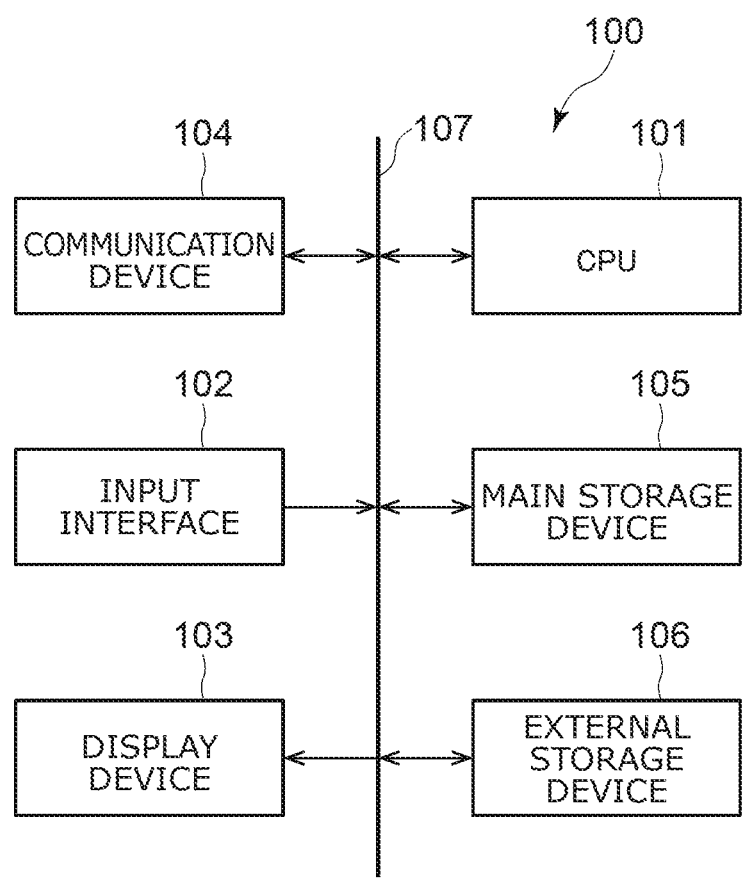
FIG. 2 is a schematic diagram illustrating a hardware configuration of the biological information measurement device of FIG. 1.

As illustrated in FIG. 2, the computer device 100 includes a central processing unit (CPU) 101, an input interface 102, a display device 103, a communication device 104, a main storage device 105, and an external storage device 106, which are interconnected via a bus 107.

The CPU 101 executes the measurement program on the main storage device 105. The above-described respective functional features described with reference to FIG. 1 are implemented by the CPU 101 executing the measurement program.

The input interface 102 is used to input operation signals from an input device such as a keyboard, a mouse, and a touch panel into the measurement device. The scheme of the input interface 102 includes, by way of example and is not limited to, USB and Ethernet. The motion information sensor and the $SpO_2$ sensor may be connected to the computer device 100 via the input interface 102.

The display device 103 is configured to display videos based on the video signals output from the measurement device. The display device is, by way of example and is not limited to, a liquid crystal display (LCD), a cathode-ray tube (CRT), and a plasma display panel (PDP). Information regarding the measured $SpO_2$, measurement time, and the like can be displayed by the display device 103.

The communication device 104 is a device for the measurement device to perform wired or wireless communications with an external device or devices. The information regarding the measured $SpO_2$, the measurement time, and the like can be transmitted to the external device or devices via the communication device 104. The external devices include, by way of example and are not limited to, a smartphone and a server. Output signals of the motion information sensor, the $SpO_2$ sensor, and the like may be input to the computer device 100 via the communication device 104.

The main storage device 105 is configured to store, when the measurement program is executed, the measurement program, data necessary for execution of the measurement program, data generated by the execution of the measurement program, and the like. The measurement program is deployed onto the main storage device 105 and thus executed. The main storage device 105 includes, by way of example and is not limited to, RAM, DRAM, and SRAM.

The external storage device 106 is configured to store the measurement program, the data necessary for execution of the measurement program, the data generated by the execution of the measurement program, and the like. The program and the data are read out into the main storage device 105 when the measurement program is executed. The external storage device 106 includes, by way of example and is not limited to, a hard disc, an optical disc, flash memory, and a magnetic tape.

It should be noted that the measurement program may be stored installed in advance onto the computer 100 or stored in a storage medium such as CD-ROM. Also, the measurement program may be uploaded onto the Internet.

Figure 3:
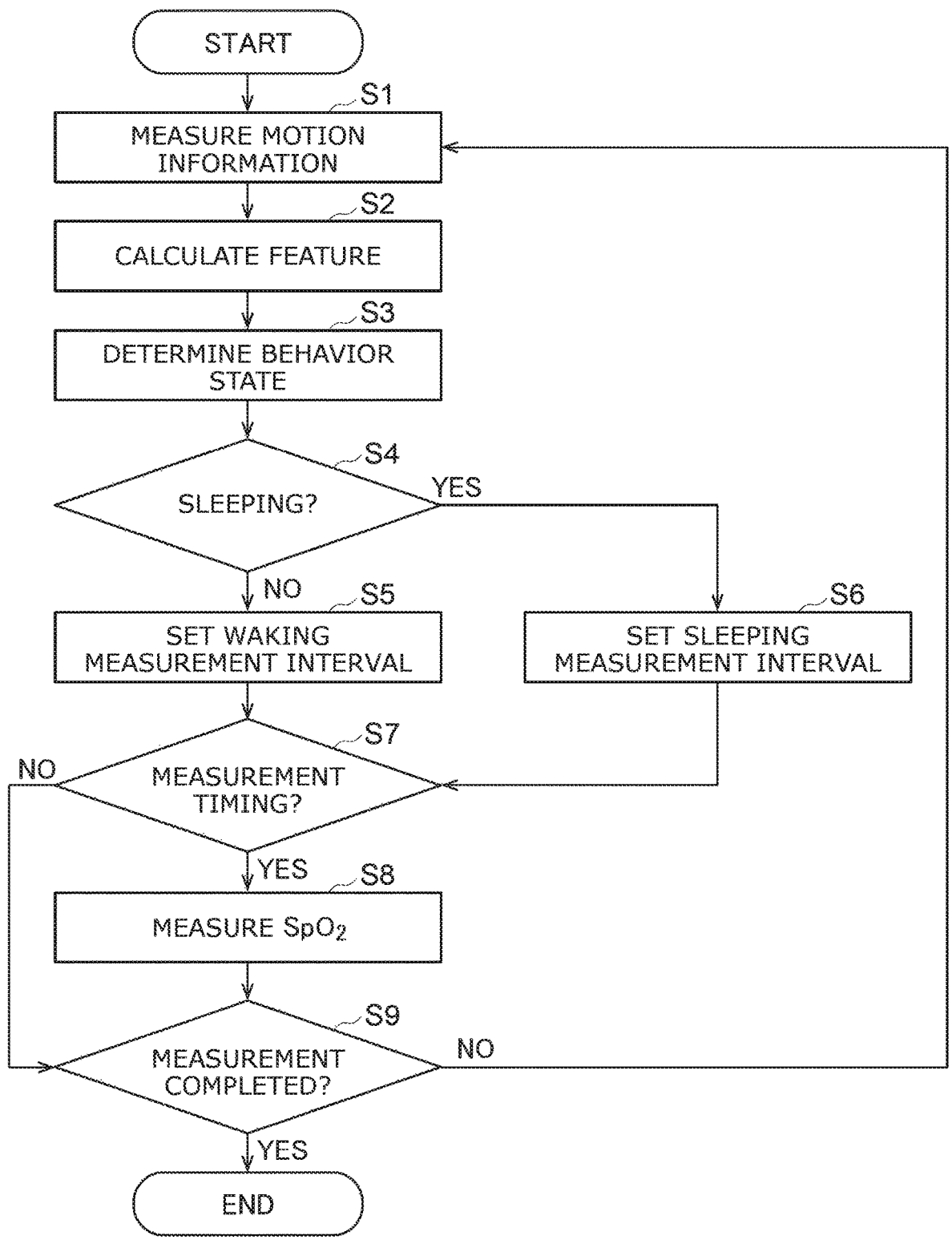
FIG. 3 is a flowchart illustrating, the operation of the biological information measurement device of FIG. 1.

Next, the operation of the measurement device in accordance with this embodiment is specifically described with reference to FIG. 3. It is assumed in the following explanations that the motion information represents the acceleration, the feature is the body motion amount, and two behavior states, i.e., sleeping and waking are considered. Nevertheless, as discussed in the foregoing, the motion information, the body motion amount, and the behavior state(s) are not limited to the considered ones. FIG. 3 is a flowchart that illustrates the operation of the measurement device in accordance with this embodiment.

As illustrated in FIG. 3, when the measurement processing by the measurement device is started, the motion information measurer 1 measures the acceleration of the user in the step S1. Specifically, the motion information measurer 1 calculates the acceleration of the user from the output signal of the acceleration sensor. The acceleration sensor is, by way of example and not limited to, a uniaxial, biaxial, triaxial, or n-axial (where "n" is a natural number) acceleration sensor. It should be noted that the measurement processing by the measurement device is started by way of example at the timing at which the power supply of the measurement device is turned on or upon reception of a start signal from the user.

In the step S2, the feature calculator 2 calculates the body motion amount of the user from the acceleration measured by the motion information measurer 1. The feature calculator 2 calculates, as the body motion amount, for example, composite acceleration such as two-axis and three-axis accelerations and an average value of the composite accelerations.

In the step S3, the behavior state determiner 3 determines the behavior state of the user from the body motion amount calculated by the feature calculator 2. Specifically, the behavior state determiner 3 determines whether or not the user is sleeping or awake. The behavior state determiner 3 can determine whether or not the user is sleeping, for example, by using a maximum value, an average value, an integrated value, pattern, and the like of the body motion amount.

When the behavior state determiner 3 has determined that the user is awake (NO in the step S4), the process goes to the step S5. When the behavior state determiner 3 has determined that the user is sleeping (YES in the step S4), the process goes to the step S6.

If the user is awake, the measurement interval controller 4 sets the measurement interval of the SpO$_2$ measurer 5 to the measurement interval during waking (first measurement interval) in the step S5. The measurement interval during waking is, for example, any appropriate interval not shorter than one minute and not longer than 60 minutes.

Control of the measurement interval by the measurement interval controller 4 may be performed by controlling the detection interval of the SpO$_2$ sensor or may be performed by controlling the interval at which SpO$_2$ is calculated from the output signal of the SpO$_2$ sensor.

In contrast, if the user is sleeping, the measurement interval controller 4 sets the measurement interval of the SpO$_2$ measurer 5 to the measurement interval during sleeping (second measurement interval) in the step S6. The measurement interval during sleeping is an interval that is shorter than the measurement interval during waking and is any appropriate interval not shorter than one second and not longer than 10 seconds. Setting the measurement interval during sleeping in this manner makes it possible to perform accurate diagnosis of SAS, the reason for which is as follows.

A method that uses apnea hypopnea index (AHI) is known as the method for diagnosis of SAS. AHI is the number of apneas or hypopneas per hour. Apnea is suspension of breathing for 10 seconds or more. Hypopnea is 3% (or greater) reduction in SpO$_2$ continued for at least 10 seconds. Apneas and hypopneas can be detected by measuring SpO$_2$.

If the measurement interval during sleeping is longer than 10 seconds, it may happen that apnea and/or hypopnea occur during the waiting period of the measurement, which means that they cannot be detected. In contrast, if the measurement interval during sleeping is equal to or shorter than 10 seconds, it is possible to measure SpO$_2$ at least once while the apnea and the hypopnea are occurring. In other words, it is made possible to suppress the possibility of failure to detect apneas and hypopneas. As a result, accurate measurement of AHI and accurate diagnosis of SAS can be performed by setting the measurement interval during sleeping to be equal to or shorter than 10 seconds.

It should be noted that the measurement interval during sleeping should be preferably set to be, for example, 10 seconds. The measurement interval in this context is a non-operating time of the SpO$_2$ sensor, and is not the time in which the SpO$_2$ sensor operates to calculate SpO$_2$. Since SpO$_2$ is to be calculated during the SpO$_2$ sensor operating time, the SpO$_2$ sensor operates for example for five seconds and calculates SpO$_2$ using the pulse during the five seconds. By virtue of this, it is made possible to increase accuracy of diagnosis of SAS and reduce the power consumption of the measurement device.

As another method of setting the operating time (measurement time) and the non-operating time (measurement interval) of the SpO$_2$ sensor, the following method may be considered. First, the time corresponding to consecutive 3 to 7 pulses of a wearer is calculated from the number of pulses of the wearer per predetermined time, and the calculated time is defined as the operating time. Further, the non-operating time is defined as a period of time one-and-a-half to two-and-a-half times as long as the operating time. By virtue of this, it is made possible to achieve accurate measurement that takes into account the individual differences of wearers.

After the measurement interval controller 4 has set the measurement interval in the step S5 or S6, the process goes to the step S7.

In the step S7, the SpO$_2$ measurer 5 determines whether or not the current time is the measurement timing of SpO$_2$. If the current time is the measurement timing (YES in the step S7), the process goes to the step S8. If it is not the measurement timing (NO in the step S7), the process goes to the step S9.

When the measurement timing has arrived, the SpO$_2$ measurer 5 measures SpO$_2$ in the step S8. Specifically, the SpO$_2$ measurer 5 irradiates the measurement site with the R light and the IR light by the SpO$_2$ sensor; acquires a signal from the light reception section that receives the transmitted or reflected light thereof; and calculates SpO$_2$ from the acquired signal.

Following the step S8, or when the measurement timing has not arrived in the step S7, the process goes to the step S9.

In the step S9, the measurement device determines whether or not the measurement processing should be terminated. If the measurement processing should be terminated (YES in the step S9), the measurement device stops the operation of the above-described respective functional features and terminates the measurement processing. The measurement processing by the measurement device is terminated, by way of example, at the timing at which the power supply to the measurement device is turned off or upon reception of an end signal from the user.

In contrast, when the measurement processing should not be terminated (NO in the step S9), the process goes back to the step S1. Thereafter, the measurement device repeats the above-describe processing steps S1 to S9 until the measurement processing is terminated.

As has been described in the foregoing, since the measurement device in accordance with this embodiment intermittently measures $SpO_2$, it is made possible to reduce its power consumption. As a result, it is made possible to achieve extended continuous operation of the measurement device and downsizing of the battery.

Also, since the measurement device measures $SpO_2$ at the measurement intervals not longer than 10 seconds while the user is sleeping, it is made possible to detect apneas and hypopneas occurring during sleeping without overlooking any one of them. Accordingly, use of the measurement device allows for accurate diagnosis of SAS.

It should be noted that the measurement device in accordance with this embodiment may be configured as one single wearable device or may be configured as a system constituted by multiple devices interconnected by wired or wireless connections.

When the measurement device is to be configured as a system constituted by multiple devices, the system can be configured, for example, by a sensor unit 20 and an information processing terminal 30. The sensor unit 20 is configured by way of example by a wearable device of bracelet type, finger ring type, or sticker type. Also, the information processing terminal 30 is configured by way of example by a sensor hub, smartphone, or dedicated terminal.

Figure 4:
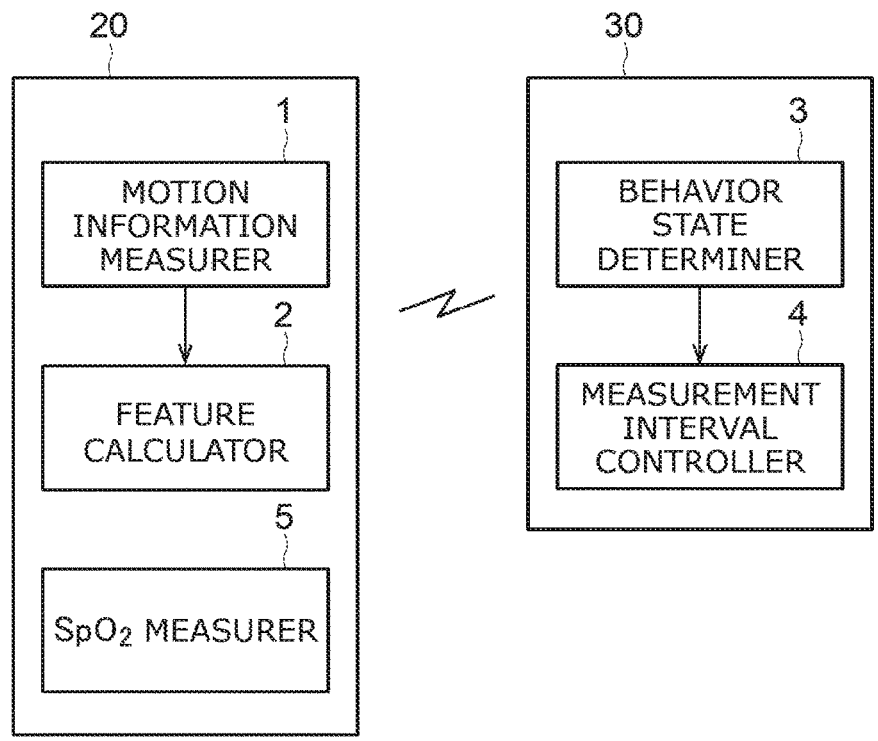
FIG. 4 is a schematic diagram illustrating one example of the biological information measurement device of FIG. 1.

As illustrated in FIG. 4, it is preferable that the sensor unit 20 includes the motion information measurer 1, the feature calculator 2, and the $SpO_2$ measurer 5. Also, it is preferable that the information processing terminal 30 includes the behavior state determiner 3 and the measurement interval controller 4. In this case, the information processing terminal 30 determines the behavior state of the user on the basis of the feature received from the sensor unit 20, and generates the control signal of the measurement interval of $SpO_2$ on the basis of the behavior state. The sensor unit 20 of the measurement interval of $SpO_2$ is thus controlled by the control signal received by the sensor unit 20 from the information processing terminal 30. By virtue of this configuration, it is made possible to reduce the power consumption of the sensor unit 20.

Figure 5:
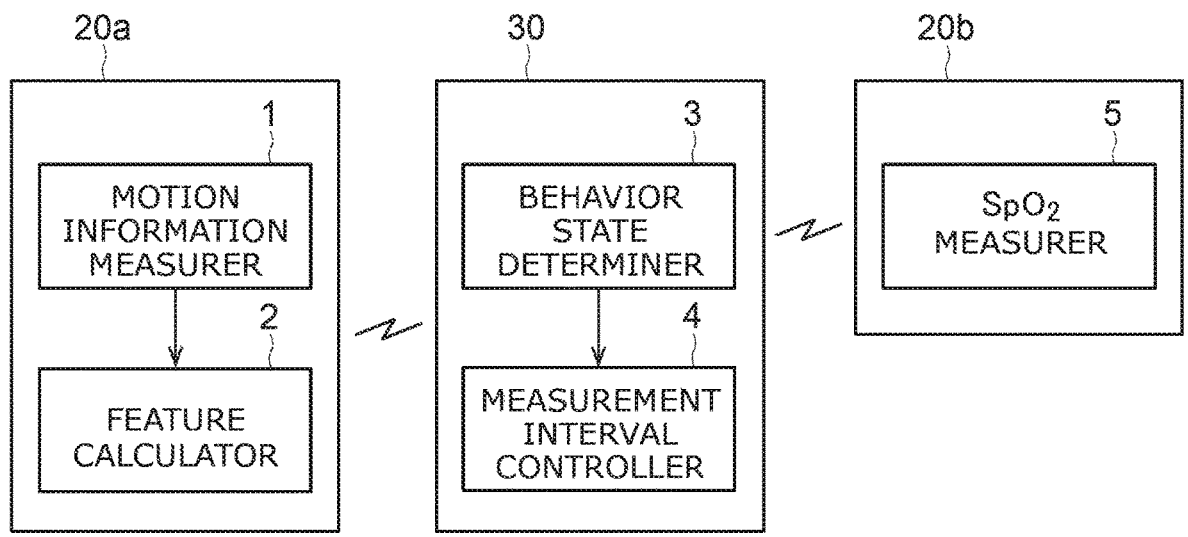
FIG. 5 is a schematic diagram illustrating another example of the biological information measurement device of FIG. 1.

Also, the system may be configured, as illustrated in FIG. 5, by a first sensor unit 20a that includes the motion information measurer 1 and the feature calculator 2, a second sensor unit 20b that includes the $SpO_2$ measurer 5, and the information processing terminal 30 that includes the behavior state determiner 3 and the measurement interval controller 4. When the system is configured in this manner, it is made possible to attach the motion information measurer 1 and the $SpO_2$ measurer at their respective locations appropriate for their measurements.

Figure 6:
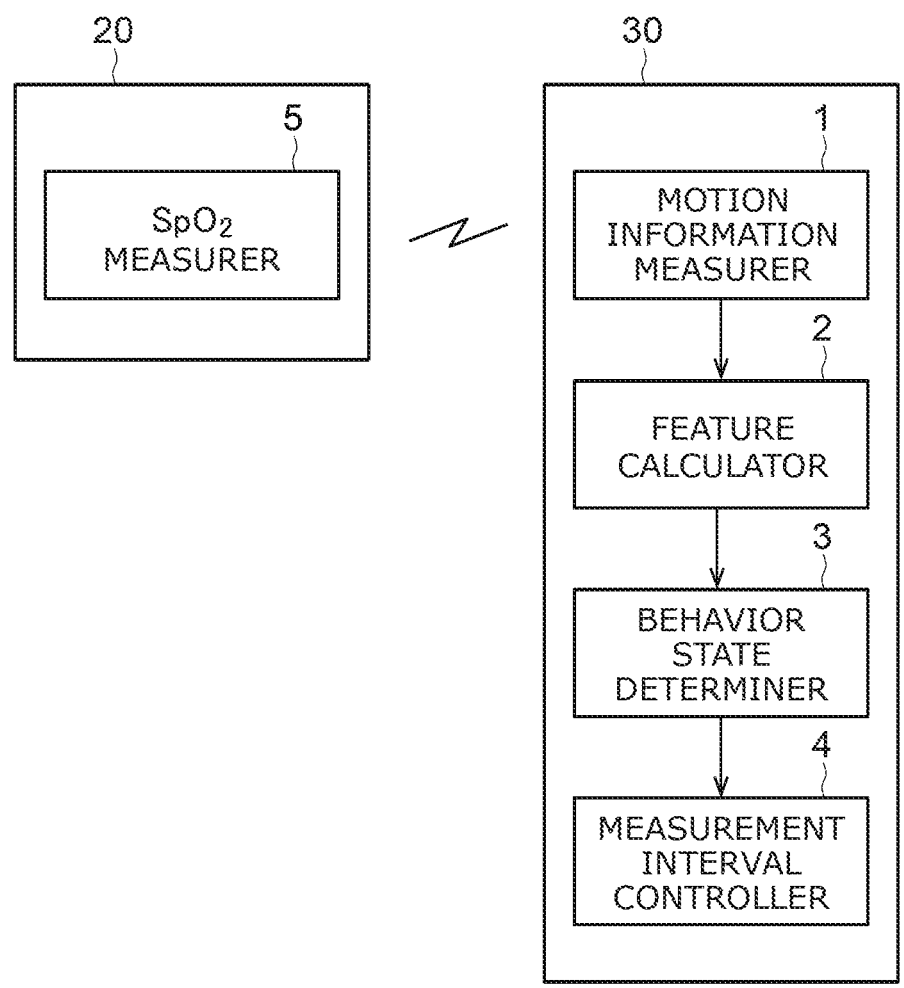
FIG. 6 is a schematic diagram illustrating yet another example of the biological information measurement device of FIG. 1.

Further, as illustrated in FIG. 6, it is also possible to configure the system by the information processing terminal 30 that includes the motion information measurer 1, the feature calculator 2, the behavior state determiner 3, and the measurement interval controller 4; and the sensor unit 20 that includes the $SpO_2$ measurer 5.

It should be noted that a program or programs that realizes the respective functional features of the behavior state determiner 3 and the measurement interval controller 4 may be installed on the information processing terminal 30 in advance, or the program(s) may be downloaded via the Internet.

Second Embodiment

Figure 7:
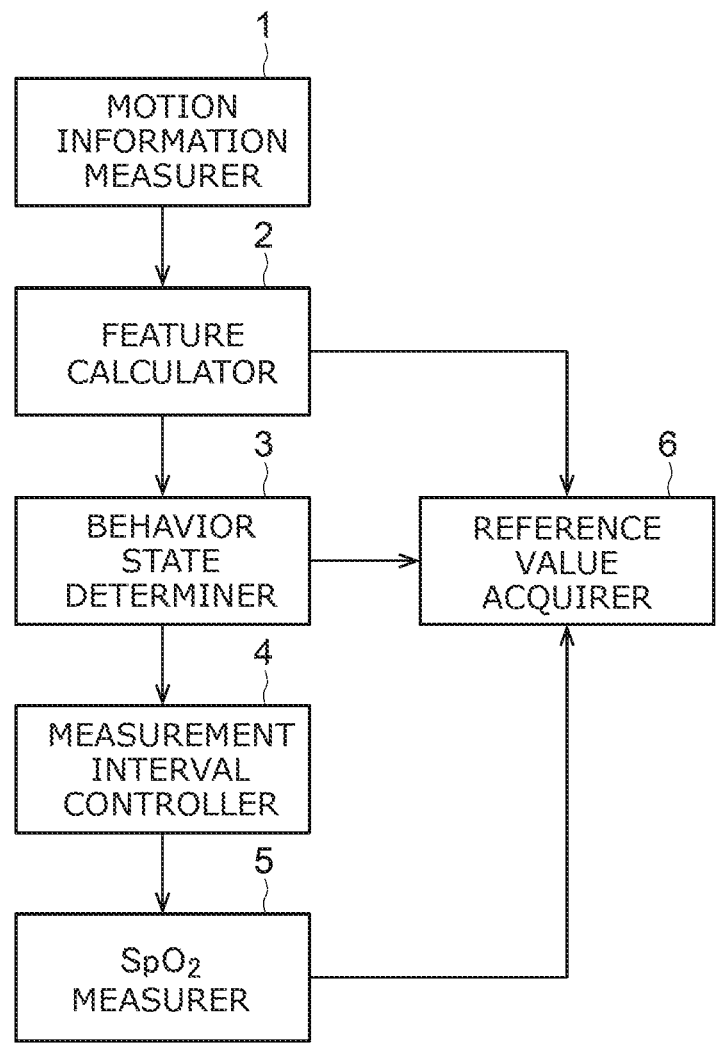
FIG. 7 is a schematic diagram illustrating a functional configuration of a biological information measurement device in accordance with a second embodiment.

The measurement device and the measurement program in accordance with a second embodiment are described with reference to FIGS. 7 to 11. FIG. 7 is a schematic diagram that illustrates the functional configuration of the measurement device in accordance with this embodiment. As illustrated in FIG. 7, the measurement device further includes a reference value acquirer 6. The functional feature of the reference value acquirer 6 is realized by the computer device 100 executing the measurement program. The remaining features are the same as those in the first embodiment.

The reference value acquirer 6 is configured to acquire a reference value of $SpO_2$ of the user. The reference value of $SpO_2$ is the $SpO_2$ of the user in the normal state. The decrease rate of $SpO_2$ used in detection of apnea and hypopnea can be calculated as a decreasing rate with reference to the reference value.

The reference value acquirer 6 is configured to acquire as the reference value the $SpO_2$ measured by the reference value acquisition period. The reference value acquisition period is a period of time predefined in advance as a period that is suitable for acquisition of the reference value. The reference value acquisition period is specified based on at least either of the behavior state and the feature of the user.

The reference value acquisition period is, for example, a period during which the behavior state of the user is determined as "sleeping" by the behavior state determiner 3. This is because the body motion of the user occurs less frequently while the user is sleeping, and such a period of time is suitable for the acquisition of the reference value.

Figure 8:
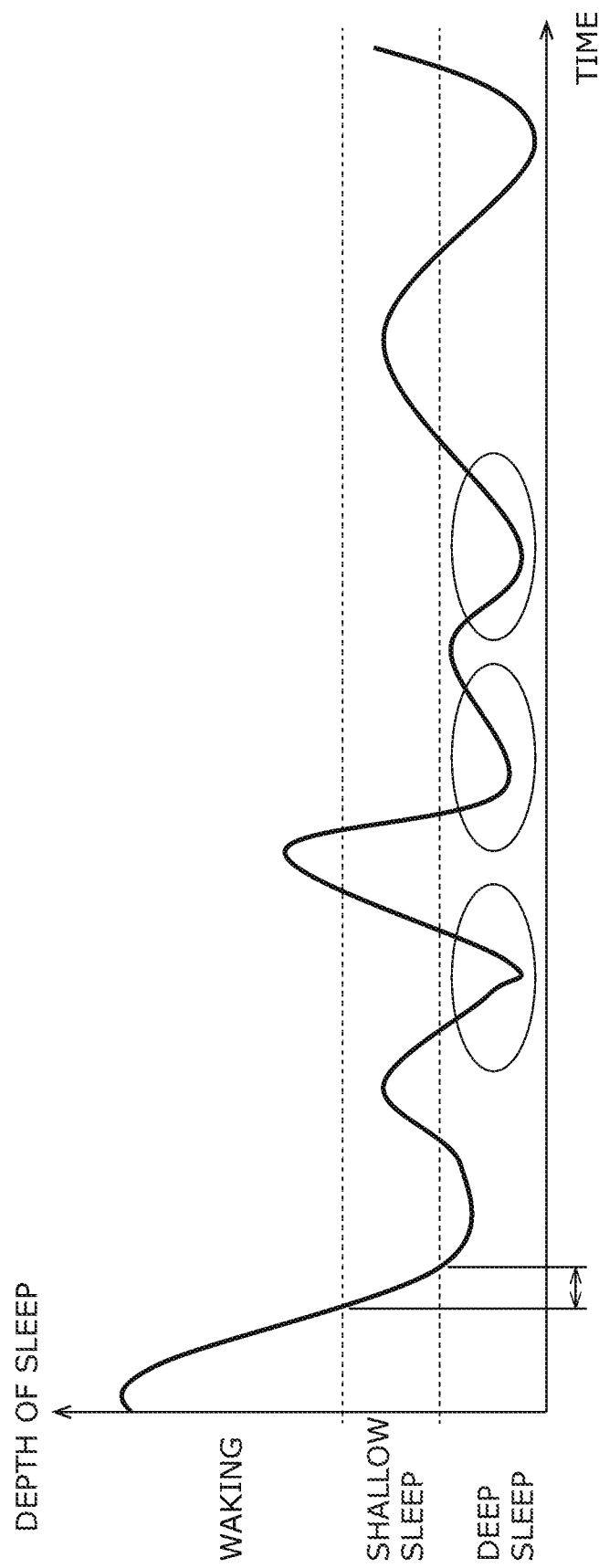
FIG. 8 is a diagram for explanation of one example of a reference value acquisition period.
Figure 9:
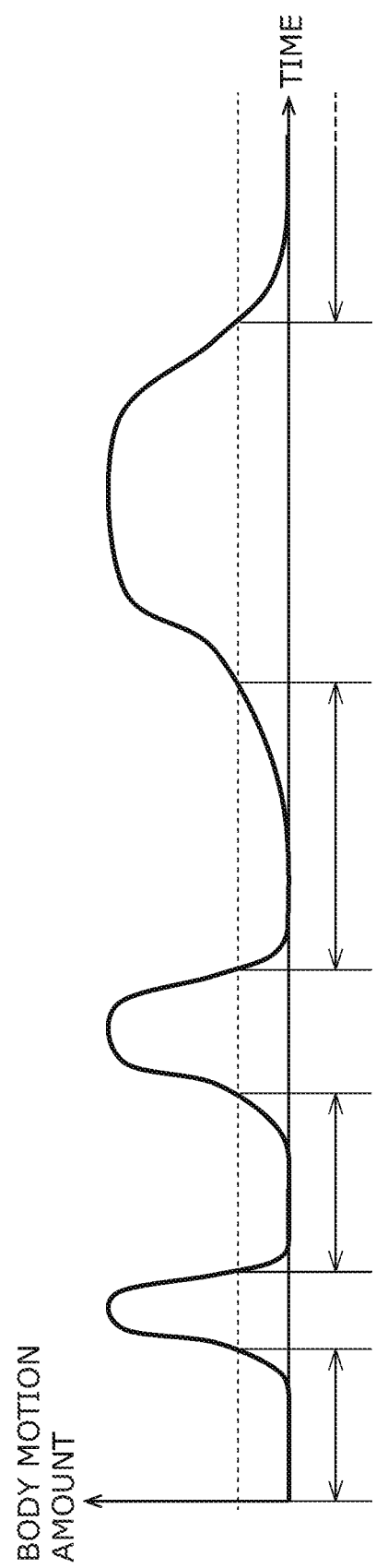
FIG. 9 is a diagram for explanation of another example of the reference value acquisition period.

Also, it is preferable that the reference value acquisition period is a period of the first shallow sleep after the user falling asleep among the periods in which the behavior state is determined as "sleeping." This is because $SpO_2$ tends to be easily decreased in the period of shallow sleep (the circled periods in FIG. 8) whilst $SpO_2$ rarely exhibit extreme decrease in the period of the first shallow sleep after the user falling asleep (the period indicated by the arrow in FIG. 8). If the period of the first shallow sleep after the user falling asleep is defined to be the reference value acquisition period, then it is preferable that the behavior state determiner 3 determines both the shallow sleep and the deep sleep respectively as the behavior states. The shallow sleep corresponds to, for example, REM sleep and the deep sleep corresponds to, for example, Non-REM sleep.

Further, the reference value acquisition period may be a period in which the body motion amount is equal to or smaller than a predetermined value among, the periods in which the behavior state of the user is determined as "waking" by the behavior state determiner 3. This is because a period in which the body motion amount is small (the period indicated by the arrow in FIG. 9) is suitable for acquisition of reference value even when the user is awake.

Still further, the reference value acquisition period may be a period in which the behavior state of the user determined by the behavior state determiner 3 is a behavior state in which the body motion is expected to be less frequent. The behavior state in which the body motion is less frequent includes, by way of example and is not limited to, walking, riding on a train, car, or bus, being aboard an airplane, being aboard a ship, dining, drinking and eating, doing desk work, lying in a supine position, and being seated.

Figure 10:
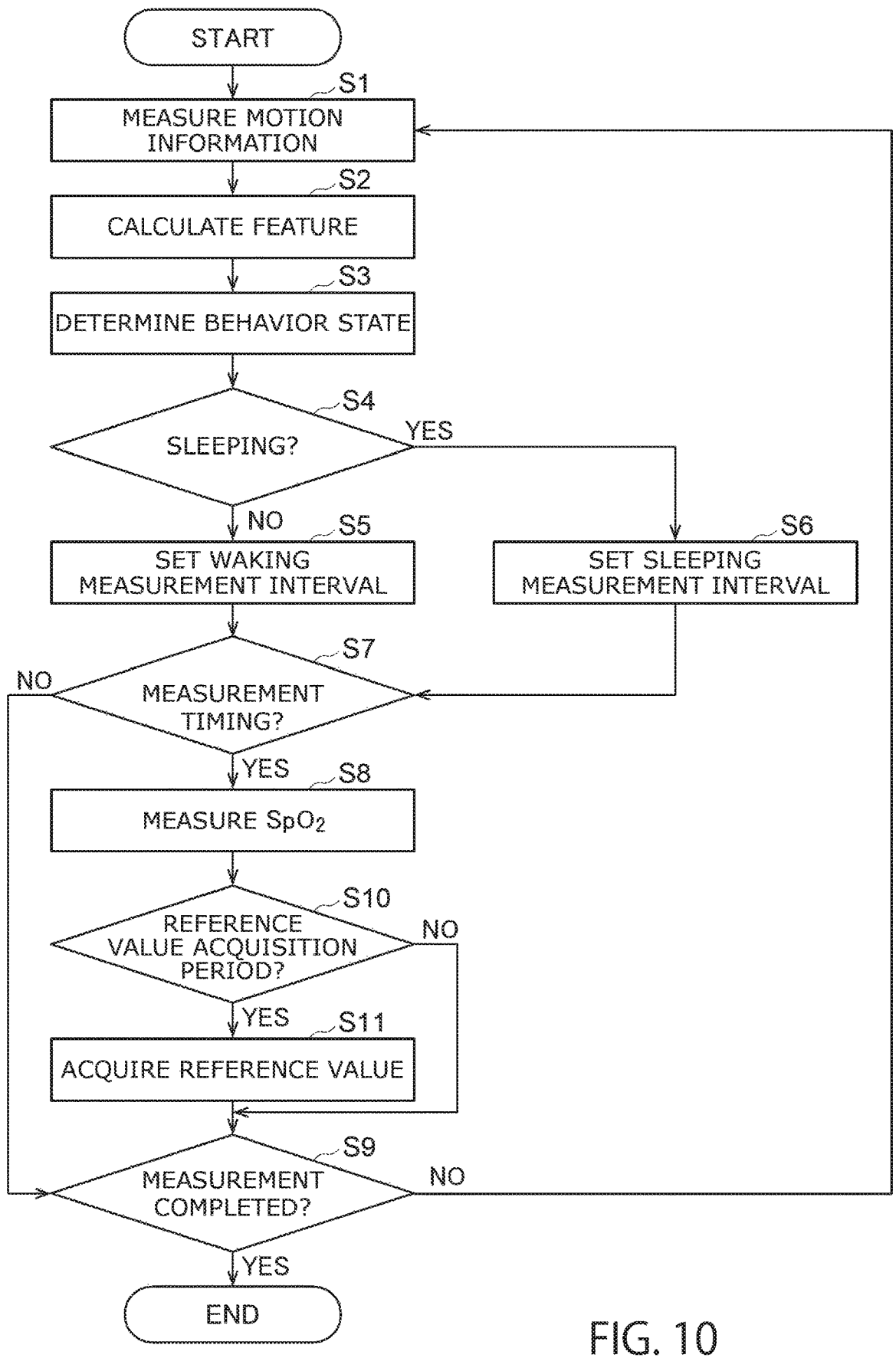
FIG. 10 is a flowchart illustrating the operation of the biological information measurement device of FIG. 7.

Next, the operation of the measurement device in accordance with this embodiment is specifically described with reference to FIG. 10. FIG. 10 is a flowchart that illustrates the operation of the measurement device. The steps S1 to S9 in FIG. 10 are the same as those in the first embodiment. In this embodiment, after the step S8, the process goes to the step S10.

In the step S10, the reference value acquirer 6 acquires at least either of the feature and the behavior state, and determines whether or not the current time is within the reference value acquisition period. If the current time is not within the reference value acquisition period (NO in the step S10), the process goes to the step S9.

In contrast, if the current time is within the reference value acquisition period (YES in the step S10), the reference value acquirer 6 acquires the $SpO_2$ measured in the step S8 from the $SpO_2$ measurer 5. The reference value acquirer 6 stores the acquired $SpO_2$ as the reference value. After that, the process goes to the step S9.

Figures 11, 12:
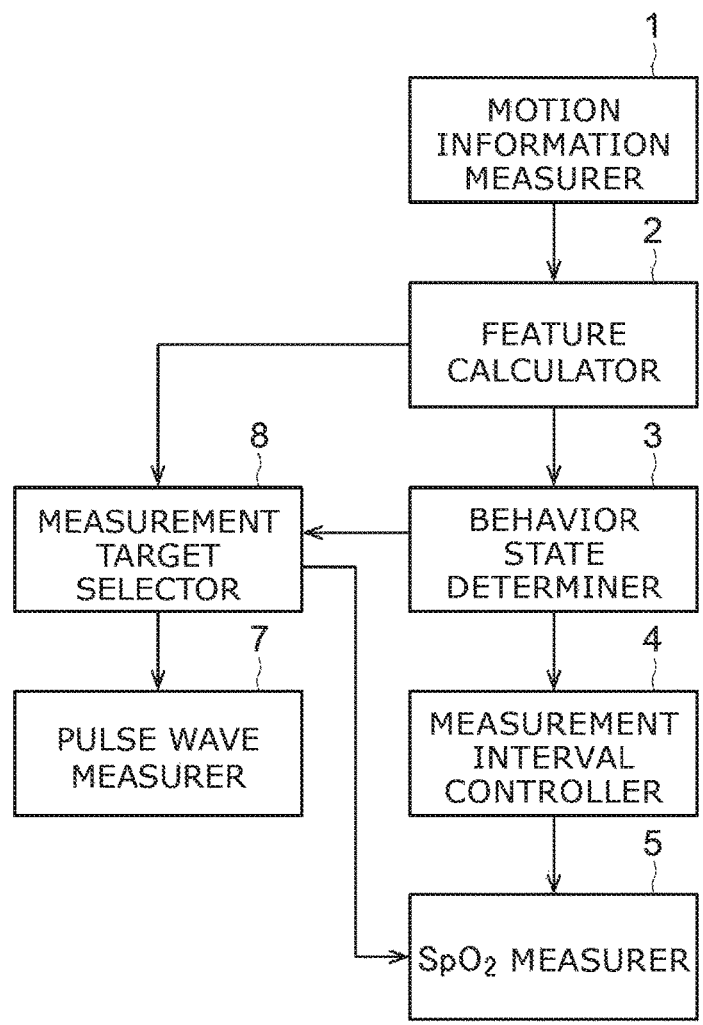
FIG. 11 is a diagram illustrating an example of a result of measurement by the biological information measurement device of FIG. 7.
FIG. 12 is a diagram illustrating a functional configuration of a biological information measurement device in accordance with a third embodiment.

FIG. 11 is a diagram that illustrates an example of the results of measurement of $SpO_2$ by the measurement device. Referring to FIG. 11, each measurement result includes the time at which the measurement was performed (which is hereinafter referred to as "measurement time), the behavior state at the measurement time, the measured $SpO_2$ ($SpO_2$ value), the reference value (reference $SpO_2$), and a reference value flag. The reference value flag indicates whether or not $SpO_2$ measured at that time is a reference value. The measurement device stores the measurement results as described here associated with the respective measurement times.

As has been described in the foregoing, the measurement device in accordance with this embodiment can acquire the reference value of $SpO_2$ on the basis of the feature and the behavior state. Since the decrease rate of $SpO_2$ with reference to the reference value is used as the decrease rate of $SpO_2$ when performing diagnosis of SAS, it is made possible to more accurately determine the apnea and hypopnea which tend to exhibit individual differences. As a result, it is made possible to further increase the accuracy of diagnosis of SAS by using the measurement device in accordance with this embodiment.

Third Embodiment

The measurement device and the measurement program in accordance with a third embodiment are described with reference to FIGS. 12 to 14. FIG. 12 is a schematic diagram that illustrates the functional configuration of the measurement device in accordance with this embodiment. As illustrated in FIG. 12, the measurement device further includes a measurement target selector 7 and a pulse wave measurer 8. The functional features of the pulse wave measurer 7 and the measurement target selector 8 are realized by the computer device 100 executing the measurement program. The remaining features are the same as in the first embodiment.

The pulse wave measurer 7 is configured to measure pulse waves of the user intermittently with predetermined time intervals. The measurement interval of the pulse wave measurer 7 can be specified as appropriate. The measurement interval of the pulse wave should desirably be specified independently of the measurement interval of $SpO_2$. The examples of the measurement interval of the pulse wave may involve the following methods. According to one exemplary method, a 30-second sleep period is defined following the measurement that lasts for 30 seconds, and the pulse wave in one minute is calculated from the doubled measurement result value. According to another exemplary method, four-minute sleep period is defined following the measurement that lasts for one minute, and the measurement result is defined on an as-is basis as the pulse wave in the entire five minutes. According to still another exemplary method, a nine-minute sleep period is defined after the measurement that lasts one minute, and the measurement result is defined on an as-is basis as the pulse wave in the entire 10 minutes. These modes of setting of the measurement period and the sleep period may be designed as appropriate in accordance with the applications of the biological information measurement device. The pulse wave measurer 7 includes a pulse wave sensor and generates the pulse wave from the output signal of the pulse wave sensor. The pulse wave measurer 7 may calculate the pulse from the generated pulse wave.

The pulse wave sensor includes a G light source adapted to emit a green light (G light) and a light reception section. G light source is by way of example an LED and is adapted to irradiate the measurement site with the G light. The light reception section is by way of example a photoelectric element and is adapted to receive the light transmitted through or reflected by the measurement site and output a signal in accordance with its intensity. The light reception section of the pulse wave sensor may be shared with the $SpO_2$ sensor to be used on an as-is basis as the light reception section of the latter sensor.

The measurement target selector 8 is configured to select a target of measurement to be measured by the measurement device on the basis of at least either of the feature and the behavior state of the user. In this embodiment, there are two targets of measurement, i.e., $SpO_2$ and pulse wave. The measurement target selector 8 causes the $SpO_2$ measurer 5 to operate when $SpO_2$ is selected as the target of measurement. The measurement target selector 8 causes the pulse wave measurer 7 to operate when the pulse wave is selected as the target of measurement. Accordingly, the target of measurement selected by the measurement target selector 8 is measured according to the measurement device in accordance with this embodiment.

The measurement target selector 8 selects the target of measurement, for example, on the basis of the body motion amount. Specifically, the measurement target selector 8 compares a first threshold and a second threshold (which is larger than the first threshold) of the body motion amount with the body motion amount calculated by the feature calculator 2, and selects the target of measurement. The first threshold is an upper limit value of the body motion amount at which $SpO_2$ can be accurately measured, and the second threshold is an upper limit of the body motion amount at which the pulse wave can be accurately measured. The reason why the second threshold is larger than the first threshold is that the pulse wave is more robust to the body motion than $SpO_2$, in other words, decrease in the measurement accuracy of the pulse wave due to the body motion is less serious than that of $SpO_2$.

In the following explanations, the fact that the body motion amount is equal to or smaller than the first threshold is stated as: "The body motion amount is small." Also, the fact that the body motion amount is larger than the first threshold and equal to or smaller than the second threshold is stated as: "The body motion amount is of the intermediate level." Further, the fact that the body motion amount is larger than the second threshold is stated as: "The body motion amount is large."

Figure 13:
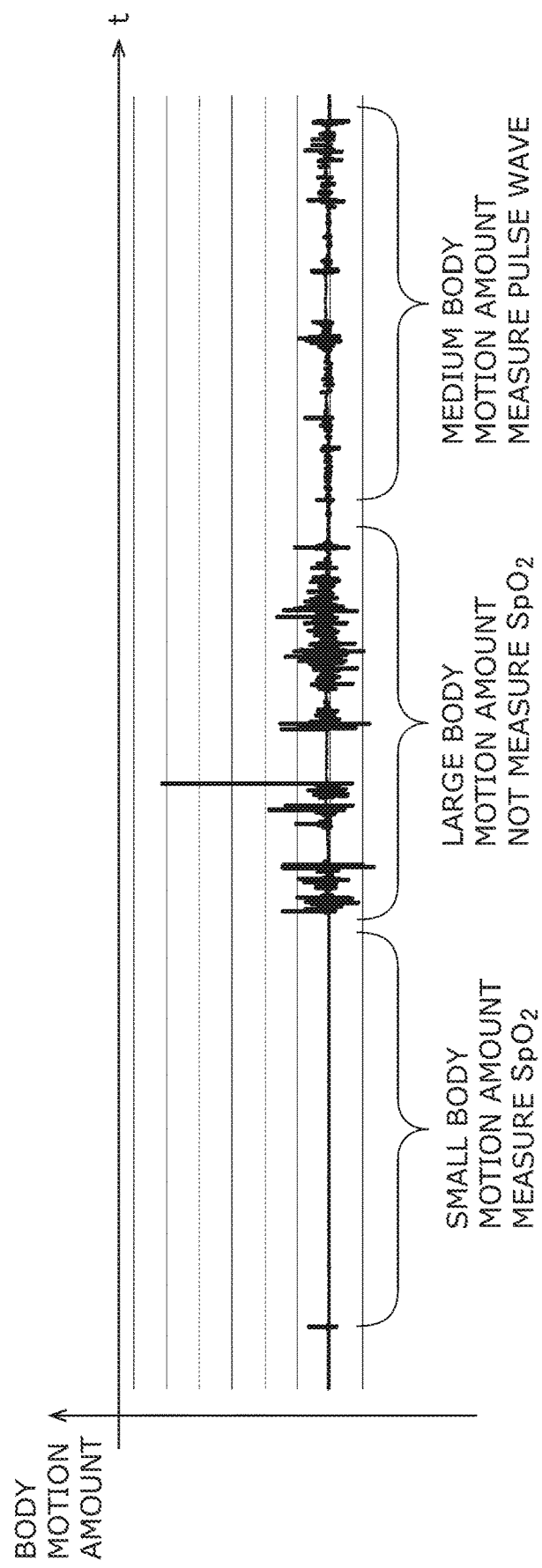
FIG. 13 is a diagram for explanation of an example of a method of determining a target of measurement.
Figure 13:
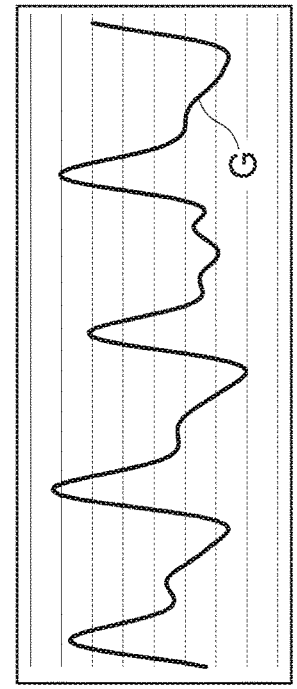
Figure 13:
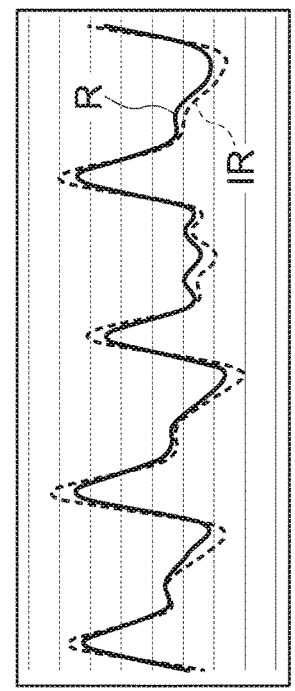
Figure 14:
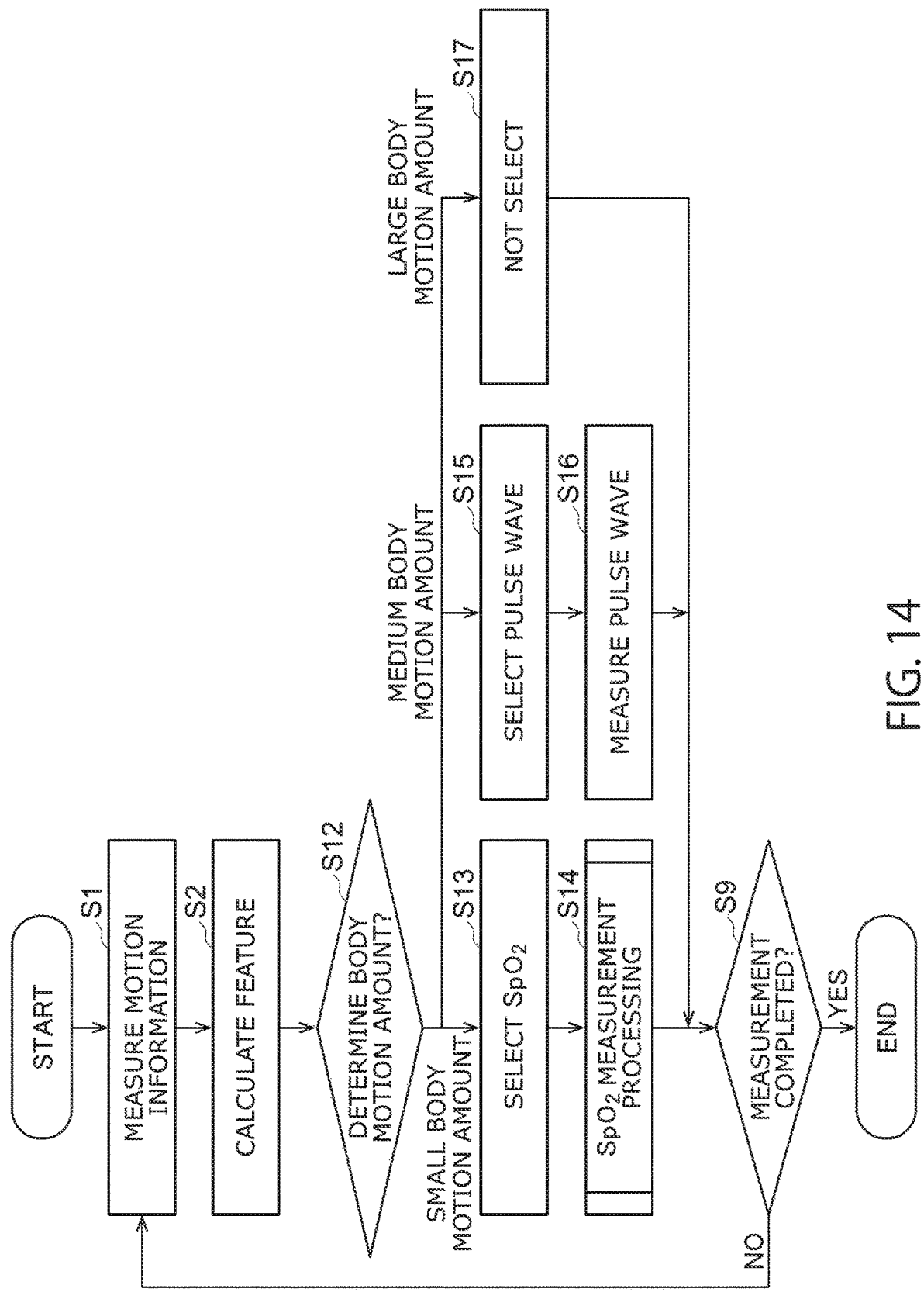
FIG. 14 is a flowchart illustrating the operation of the biological information measurement device of FIG. 12.

As illustrated in FIG. 13, the measurement target selector 8 selects $SpO_2$ as the target of measurement when the body motion amount calculated by the feature calculator 2 is small, and selects the pulse wave as the target of measurement when the body motion amount is of the intermediate level, and does not select any target of measurement when the body motion amount is large.

By selecting the target of measurement in this manner, the $SpO_2$ measurer 5 does not operate in a period of time in which the measurement accuracy of $SpO_2$ is low, and the pulse wave measurer 7 does not operate in the period of time in which the measurement accuracy of the pulse wave is low. As a result, it is made possible to reduce the power consumption of the measurement device.

It should be noted that the measurement target selector 8 may select the $SpO_2$ and the pulse wave as the targets of measurement when the body motion amount is small. This is because the pulse wave is allowed to be accurately measured when the body motion amount is small.

Also, the measurement target selector 8 may select the target of measurement on the basis of the behavior state. For example, the behavior state whose body motion amount is small; a behavior state whose body motion amount is of the intermediate level; and the behavior state whose body motion amount is large may be specified for the measurement target selector 8, and the measurement target selector 8 may compare the specified behavior state with the behavior state determined by the behavior state determiner 3 and thus select the target of measurement.

Specifically, the measurement target selector 8 selects $SpO_2$ as the target of measurement when the behavior state determined by the behavior state determiner 3 is the behavior state whose body motion amount is small; selects the pulse wave as the target of measurement when the behavior state is the behavior state whose body motion amount is of the intermediate level; and does not select any target of measurement when the behavior state is the behavior state whose body motion amount is large.

Behavior state whose body motion amount is small include, for example, sleeping, riding on a train, car, or bus, being aboard an airplane, being aboard a ship, dining, drinking and eating, doing desk work, lying in a supine position, and being seated. The behavior state whose body motion amount is of the intermediate level includes, for example, walking and bicycling. The behavior state whose body motion amount is large includes, for example, running, swimming, playing tennis, taking part in an individual sport, and taking part in a team sport. It should be noted that the classification of the behavior states is not limited to this.

Next, the operation of the measurement device in accordance with this embodiment is specifically described with reference to FIG. 14. It is assumed in the following explanations that the measurement target selector 8 selects the target of measurement on the basis of the body motion amount. FIG. 14 is a flowchart that illustrates the operation of the measurement device in accordance with this embodiment. The steps S1, S2, and S9 in FIG. 14 are the same as those in the first embodiment. In this embodiment, after the step S2, the process goes to the step S12.

In the step S12, the measurement target selector 8 determines the magnitude of the body motion amount calculated by the feature calculator 2. When the measurement target selector 8 determines that the body motion amount is small (small body motion amount), the process goes to the step S13. When the measurement target selector 8 determines that the body motion amount is of an intermediate level (medium body motion amount), the process goes to the step S15. When the measurement target selector 8 determines that the body motion amount is large (large body motion amount), the process goes to the step S17.

If the body motion amount is small, the measurement target selector 8 selects $SpO_2$ as the target of measurement in the step S13 and causes the $SpO_2$ measurer 5 to operate. At this point, the measurement target selector 8 does not cause the pulse wave measurer 7 to operate.

After that, the measurement processing of $SpO_2$ is executed in the step S14. The measurement processing of $SpO_2$ in the step S14 corresponds to the processing steps S3 to S8 in the first embodiment. After completion of the measurement processing of $SpO_2$, the process goes to the step S9.

If the body motion amount is of the intermediate level, the measurement target selector 8 selects the pulse wave as the target of measurement in the step S15 and causes the pulse wave measurer 7 to operate. At this point, the measurement target selector 8 does not cause the $SpO_2$ measurer 5 to operate. After that, the pulse wave measurer 7 measures the pulse wave in the step S16. After the measurement of the pulse wave, the process goes to the step S9.

If the body motion amount is large, the measurement target selector 8 does not select any target of measurement in the step S17. At this point, the measurement target selector 8 does not cause the $SpO_2$ measurer 5 or the pulse wave measurer 7 to operate. After that, the process goes to the step S9.

As has been described in the foregoing, according to the measurement device in accordance with this embodiment, it is made possible to measure not only $SpO_2$ but also the pulse wave. Also, since the $SpO_2$ measurer 5 and the pulse wave measurer 7 are not operated if the measurement accuracy of $SpO_2$ and the pulse wave is low, the power consumption can be reduced.

It should be noted that the measurement device in accordance with this embodiment can be configured such that it includes another biological information measurer adapted to measure biological information such as heart rate and body temperature in addition to or in place of the pulse wave measurer 7.

Fourth Embodiment

Figure 15:
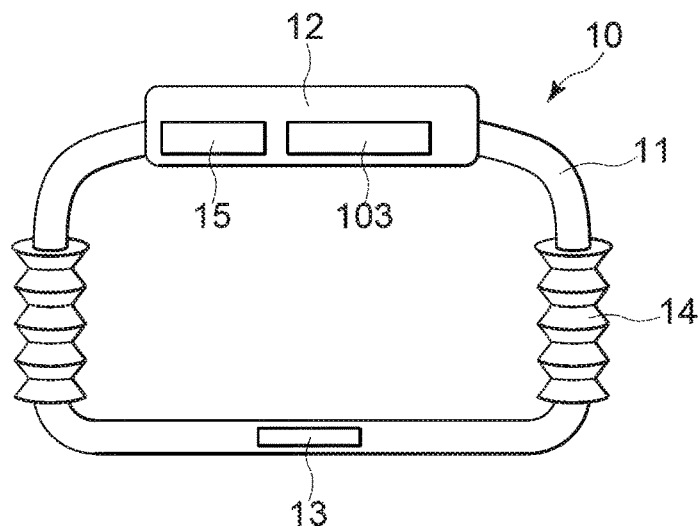
FIG. 15 is a schematic diagram illustrating a hardware configuration of a biological information measurement device in accordance with a fourth embodiment.

The measurement device in accordance with the fourth embodiment is described with reference to FIG. 15 to FIG. 17. The measurement device in accordance with this embodiment is configured as one single wearable device attached to an arm, finger, or the like of a user. The functional features of the measurement device are the same as those in the first embodiment. Here, FIG. 15 is a schematic diagram that illustrates a hardware configuration of a measurement device 10 in accordance with this embodiment. As illustrated in FIG. 15, the measurement device 10 includes a band 11, a housing 12, and an SpO2 sensor 13.

The band 11 is a ring-shaped member for attaching the measurement device 10 to an attachment location (arm, finger, and the like of the user). The user wears the measurement device 10 with his/her arm, finger, or the like passed through the band 11. The band 11 includes a bellows portion (or accordion fold portion) 14.

The bellows portion 14 is a bellows-like section formed in a part of the band 11. The bellows portion 14 is adapted to be extended and contracted in the circumferential direction of the band 11 and at least one bellows portion 14 is provided in the band 11. When the user wears the measurement device 10, the bellows portion 14 causes the band 11 to be tightened to the attachment location of the user. As a result, the band 11 is secured to the attachment location of the user.

The housing 12 is secured to a part of the band 11 and the individual components of the measurement device 10 are accommodated therein. For example, although not shown, the battery of the measurement device 10 and the computer device 100 realizing the individual functional features of the measurement device 10 are incorporated in the housing 12. As illustrated in FIG. 15, a display device 103 of the computer device 100 is arranged on the outer side with respect to the band 11 such that the user can view the display device 103 while the user wears the measurement device 10.

Also, a motion information sensor 15 such as an acceleration sensor is provided on the housing 12. The motion information sensor 15 is connected inside of the housing 12 to the computer device 100 via a wiring connection. The functional features of the motion information measurer 1 are realized by cooperation of the motion information sensor 15 and the computer device 100.

The $SpO_2$ sensor 13 is a reflection-type $SpO_2$ sensor and provided on the inner circumference side of the band 11. As a result, when the user wears the measurement device 10, the $SpO_2$ sensor 13 is brought into proximity to the attachment location of the user, so that it is made possible to measure $SpO_2$ by a reflected light.

Figure 16A:
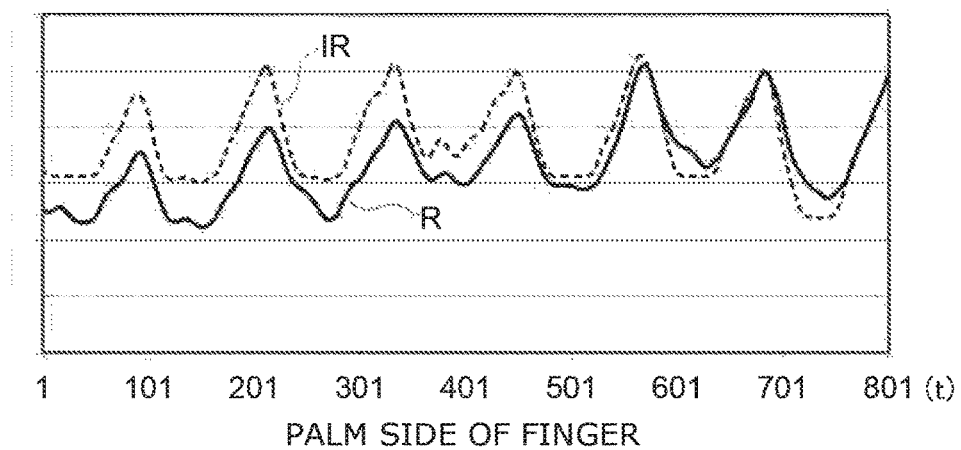
FIG. 16A and FIG. 16B each is a schematic diagram illustrating a result of measurement of $SpO_2$.
Figure 16B:
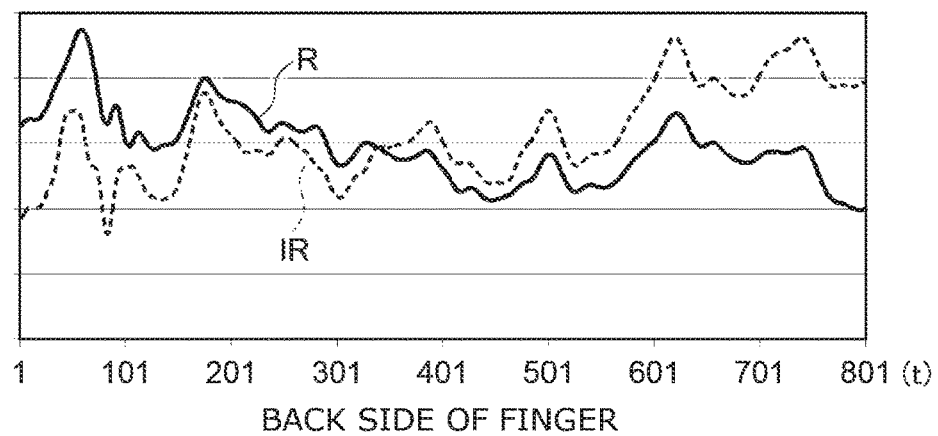

Here, FIG. 16 is a diagram that illustrates an example of the result of measurement of the reflection type $SpO_2$ sensor. FIG. 16(a) is the result of measurement of $SpO_2$ measured on the palm side of the finger whilst FIG. 16(b) is the result of measurement of $SpO_2$ measured on the back side of the finger. As can be appreciated from FIG. 16, $SpO_2$ measured on the palm side of the finger allows for more accurate detection of the heart rate than $SpO_2$ measured on the back side of the finger and leads to clear comprehension of the ratio of the extinction degrees of the R light and the IR light. This also applies to a case where $SpO_2$ is measured on an arm.

As a consequence, it is preferable that the measurement device 10 is attached such that the $SpO_2$ sensor 13 is positioned on the palm side of the finger or arm. It is also preferable that the measurement device 10 is worn by the user such that the housing 12 is positioned on the back side of the finger or arm so as to ensure increased visibility of the display device 103. In view of these aspects, as illustrated in FIG. 15, it is preferable that the $SpO_2$ sensor 13 is provided on the opposite side of the band 11 with respect to the housing 12. By virtue of this, it is made possible to simultaneously increase the measurement accuracy of $SpO_2$ and the visibility of the display device 103.

When the $SpO_2$ sensor 13 is arranged in this manner, the $SpO_2$ sensor 13 is connected to the computer device 100 via the wiring connection provided inside of the band 11. The $SpO_2$ measurer 5 is configured by the cooperation of the $SpO_2$ sensor 13 and the computer device 100.

Figure 17:
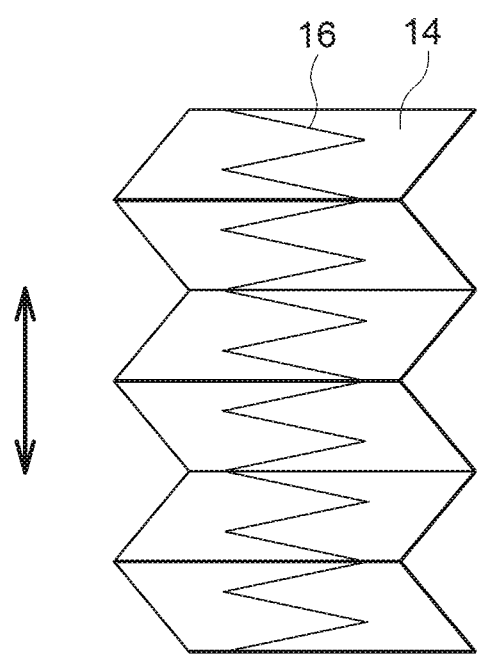
FIG. 17 is a partial enlarged view illustrating a wiring connection of a bellows portion.

Here, FIG. 17 is a partial enlarged view that illustrates the wiring connection 16 provided in the bellows portion 14 among the wiring connections of the $SpO_2$ sensor 13. Referring to FIG. 17, the arrow indicates the direction of extension and contraction of the bellows portion 14. As illustrated in FIG. 17, the wiring connection 16 is provided so as to be inclined with respect to the direction of extension and contraction of the bellows portion 14. When the wiring connection 16 is provided in this manner, the load acting upon the wiring connection 16 when the bellows portion 14 is extended is reduced compared with a case where the wiring connection 16 is provided in parallel with the direction of extension and contraction, so that it is made possible to prevent breakage of the wiring connection 16 due to the extension and contraction of the bellows portion 14.

As has been described in the foregoing, according to the measurement device 10 in accordance with this embodiment, the band 11 can be secured to the attachment location by the bellows portion 14. In other words, the $SpO_2$ sensor 13 can be secured to the measurement site such as an arm and finger. As a result, in contrast to the state of the art pulse oxymeter, it is not necessary to attach a probe at the end of the finger and movement of the finger is not restricted by the presence of the probe when the measurement device 10 is attached. Accordingly, in accordance with this embodiment, the comfort at the time of attachment of the measurement device 10 can be increased.

Next, an embodiment of biological information measurement device (hereinafter referred to as "measurement device") is described, which acquires utterance information or the like as the biological information.

Fifth Embodiment

The biological information measurement device (hereinafter referred to as "measurement device") and the biological information measurement system (hereinafter referred to as "measurement system") in accordance with a fifth embodiment are described with reference to FIGS. 18 to 23. The processing device and the measurement system in accordance with this embodiment calculate the utterance information regarding an utterance of a user on the basis of sound information collected by a microphone.

Figure 18:
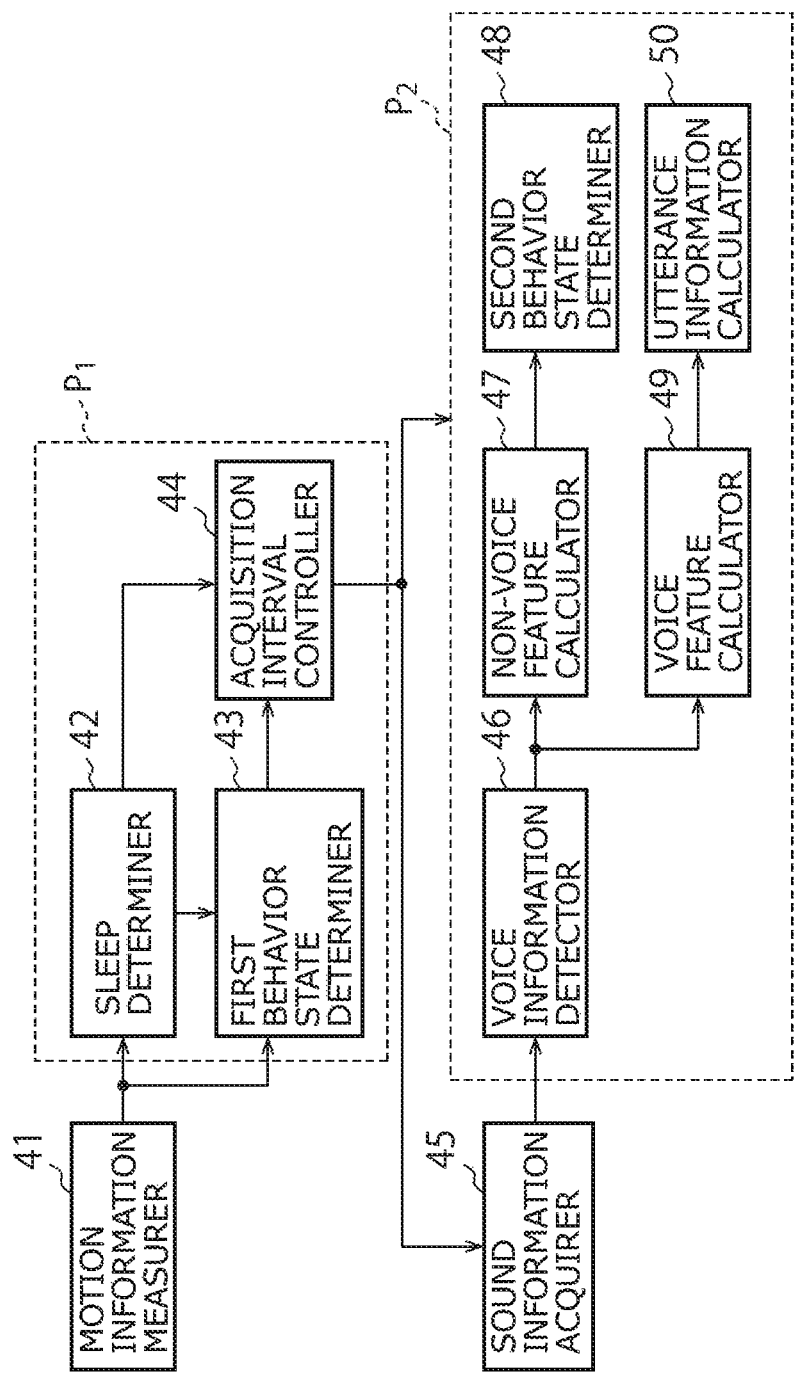
FIG. 18 is a block diagram illustrating a functional configuration of a biological information measurement device in accordance with a fifth embodiment.

First, a functional configuration of the measurement device in accordance with the fifth embodiment is described with reference to FIG. 18. The measurement device in accordance with this embodiment is configured by a device that can be attached to or carried by a user such as wearable devices and smartphones. FIG. 18 is a block diagram that illustrates the functional configuration of the measurement device.

As illustrated in FIG. 18, the measurement device includes a motion information measurer 41, a sleep determiner 42, a first behavior state determiner 43, an acquisition interval controller 44, a sound information acquirer 45, a voice information detector 46, a non-voice feature calculator 47, a second behavior state determiner 48, a sound feature calculator 49, and an utterance information calculator 50.

The motion information measurer 41 is configured to acquire the motion information of the user. The motion information represents, by way of example and is not limited to, acceleration or angular velocity. The motion information measurer 41 includes a motion information sensor adapted to detect the motion information such as an acceleration sensor and an angular velocity sensor (gyro sensor), and acquires the motion information from the output signal of the motion information sensor. The motion information measurer 41 is configured to operate continuously or intermittently with predetermined time intervals while the measurement device is operating and acquire the motion information. Also, one or more pieces of the motion information may be acquired by the motion information measurer 41.

The sleep determiner 42 (feature calculator) is configured to determine whether or not the user is sleeping on the basis of the motion information of the user acquired by the motion information measurer 41. The sleep determiner 42 calculates, for example, the feature such as the body motion amount of the user from the motion information, and is capable of determining whether or not the user is sleeping on the basis of the calculated feature.

The first behavior state determiner 43 is configured to determine the behavior state of the user on the basis of the motion information of the user acquired by the motion information measurer 41. The first behavior state determiner 43 acquires the result of determination by the sleep determiner 42 and determines the behavior state of the user only when the user is awake. Accordingly, the first behavior state determiner 43 does not operate when it has been determined by the sleep determiner 42 that the user is sleeping.

The first behavior state determiner 43 calculates the feature such as the body motion amount of the user, for example, from the motion information, and determines the behavior state of the user on the basis of the average value, variance value, maximum value, pattern, and the like of the calculated feature. The behavior state determined by the first behavior state determiner 43 includes, by way of example and is not limited to, sleeping, waking, complete standstill (processing device not being attached), walking, running, riding on a train, car, or bus, bicycling, being aboard an airplane, being aboard a ship, swimming, playing tennis, taking part in an individual sport, taking part in a team sport, dining, drinking and eating, doing desk work, lying in a supine position, and being seated.

The acquisition interval controller 44 is configured to obtain the results of determination of the sleep determiner 42 and the first behavior state determiner 43 from among multiple intermittent acquisitions having different measurement intervals, select one intermittent acquisition on the basis of the result of determination, and control the operation of the sound information acquirer 45 and the like. Specifically, the acquisition interval controller 44 stops the operation of the sound information acquirer 45 when the behavior state of the user acquired from the sleep determiner 42 and the first behavior state determiner 43 is the non-utterance state. By virtue of this, it is made possible to reduce the power consumption of the measurement device.

The non-utterance state is a behavior state specified in advance in which the user does not make any utterance or a behavior state that is not suitable for sound collection. The non-utterance state includes, by way of example and is not limited to, sleeping, complete standstill (processing device not being attached), running, bicycling, swimming, playing tennis, taking part in an individual sport, and taking part in a team sport.

In contrast, the utterance state is a behavior state specified in advance in which the user makes an utterance or a behavior state suitable for sound collection. The utterance state includes, by way of example and is not limited to, waking, walking, riding on a train, car, or bus, being aboard an airplane, being aboard a ship, dining, drinking and eating, doing desk work, lying in a supine position, and being seated. It should be noted that the utterance state may be specified as a behavior state that is not the non-utterance state.

Also, the acquisition interval controller 44 may control the operation of at least any one of the sound information acquirer 45, the voice information detector 46, the non-voice feature calculator 47, the second behavior state determiner 48, the sound feature calculator 49, and the utterance information calculator 50 on the basis of the behavior state of the user. Specifically, it is preferable that the acquisition interval controller 44 stops the operation of the above-described respective features if the behavior state of the user is the non-utterance state. By virtue of this, it is made possible to further reduce the power consumption of the measurement device.

The sound information acquirer 45 includes a microphone and is configured to intermittently acquire (perform intermittent acquisition of) the sound information around the user wearing or carrying the measurement device at predetermined time intervals. The sound information acquired by the sound information acquirer 45 includes information of sound which is a voice of a human (voice information) and information of sound other than voice (non-voice information). The acquisition interval for acquisition of the sound information by the sound information acquirer 45 can be specified as appropriate such as one-second interval and one minute interval. It should be noted that the sound information acquirer 45 may include an AD converter, a filter, an amplifier, and the like.

Figure 19:
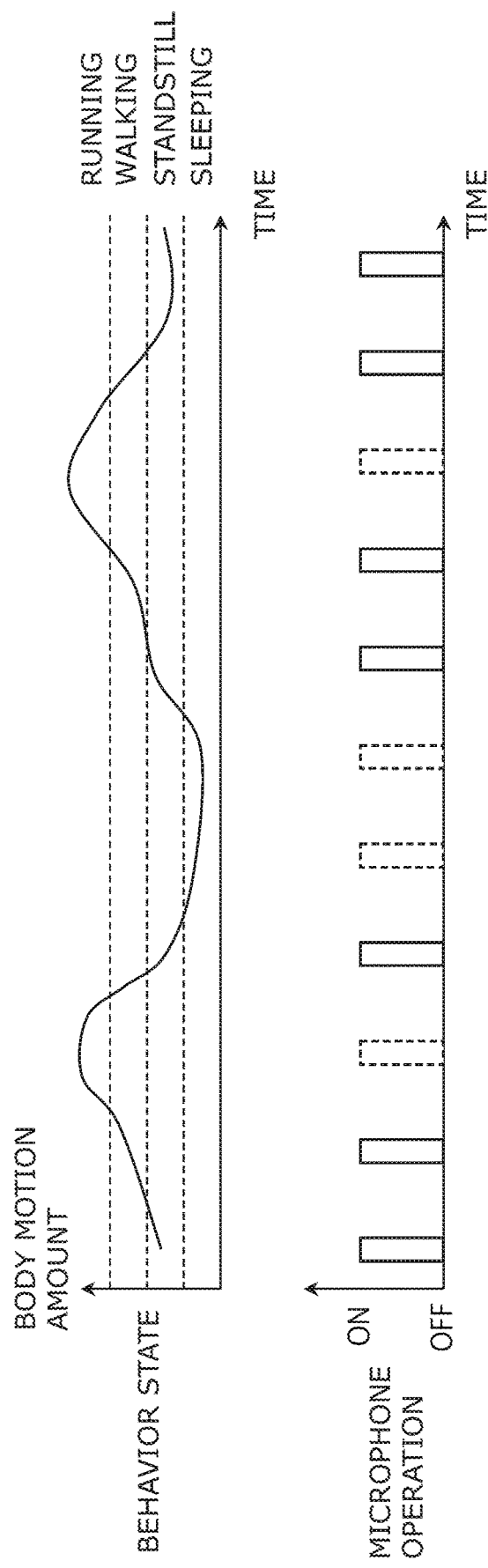
FIG. 19 is an explanatory diagram for explanation of the operation of a sound information acquirer.

Here, FIG. 19 is a diagram that illustrates an example of the operation of the sound information acquirer 45. Referring to FIG. 19, the acquisition interval controller 44 controls the operation of the sound information acquirer 45 by controlling turning on and off of the microphone. Also, "running" and "sleeping" are specified as the non-utterance states, and the acquisition interval controller 44 turns the microphone off when the user is running or sleeping. Movement speed or movement intensity may be used to discriminate running from walking. When the sound information acquirer 45 is controlled in this manner, the microphone can be turned off in the intervals indicated by the dotted lines in FIG. 19. Accordingly, it is made possible to reduce the power consumption of the measurement device compared with a case where the microphone is simply intermittently operated. It should be noted that, when the behavior state is specified in accordance with the range of the feature such as the body motion amount as illustrated in FIG. 19, the acquisition interval controller 44 may control the operation of the sound information acquirer 45 in accordance with the feature.

The voice information detector 46 is configured to detect the voice information from the sound information acquired by the sound information acquirer 45. The voice information detector 46 detects the voice information, for example, by voice activity detection (VAD). The sound information consists of the voice information and the non-voice information. Accordingly, when the voice information detector 46 detects the voice information, the sound information other than the voice information is detected as the non-voice information.

The non-voice feature calculator 47 calculates the feature of the non-voice information detected by the voice information detector 46 (hereinafter referred to as "non-voice feature"). The non-voice feature includes, by way of example and is not limited to pitch, frequency, intensity, envelope, sound spectrogram, and the like of voice. The non-voice feature is selected in accordance with the behavior state determined by the second behavior state determiner 48.

The second behavior state determiner 48 determines the behavior state of the user on the basis of the non-voice feature calculated by the non-voice feature calculator 47. Specifically, the second behavior state determiner 48 determines the behavior state of the user from the sounds around the user. For example, "A Real-time Living Activity Recognition System by Using Sensors on a Mobile Phone" (Ouchi et al., Journal of Information Processing Society of Japan (June, 2012) or the like is relied on. The behavior state determined by the second behavior state determiner 48 includes, but is not limited to, cleaning a bathroom, opening and closing a refrigerator, brushing teeth, vacuuming, watching TV, shaving, using a hair dryer, ironing, and washing dishes.

The sound feature calculator 49 is configured to calculate the feature of the voice information detected by the voice information detector 46 (hereinafter referred to as "sound feature"). The sound feature includes, by way of example and is not limited to, frequency, intensity, and sound spectrogram. The sound feature is selected in accordance with the utterance information calculated by the utterance information utterance information calculator 50.

The utterance information calculator 50 is configured to calculate utterance information on the basis of the sound feature calculated by the sound feature calculator 49. The utterance information includes, but is not limited to, a user utterance amount and a user utterance time.

The utterance information calculator 50 may store in advance, for example, an acoustic model generated from the feature of the voice of the user and carry out detection of voice intervals for the utterances of the user from the voice information on the basis of the acoustic model. For example, "Speaker Change Detection and Speaker Clustering Using VQ Distortion Measure" (Nakagawa et al., Journal of Institute of Electronics, Information and Communication Engineers D-II (November 2002) or the like may be relied on to carry out discrimination of speakers based on the feature and the acoustic model to determine whether or not any other person is included or only the utterances of the user himself/herself is included, and thereby separates the speaker's voice activities from each other. By virtue of this, voice information can be classified into the utterances of the user and the utterances of a person or persons other than the user (other persons). In this case, the utterance information calculator 50 may calculate the user utterance amount, the user utterance time, the utterance amount of the other person(s), the utterance time of the other person(s), conversation time, and proportion of the utterances of the user as the utterance information.

Also, the utterance information calculator 50 may store the acoustic models of the user for each behavior state of the user. Such acoustic models include, for example, an acoustic model of the user who is on the phone, an acoustic model of the user having face-to-face conversations with someone, and an acoustic model of the user watching TV. Since a distinctive aspect of watching TV is that it involves various music sounds and sound effects, the acoustic model is created using these features. By using the acoustic models created on a per-behavior-state basis, it is made possible to acquire the states in which the user made his/her utterance (e.g., having conversations and speaking to himself/herself).

Figure 20:
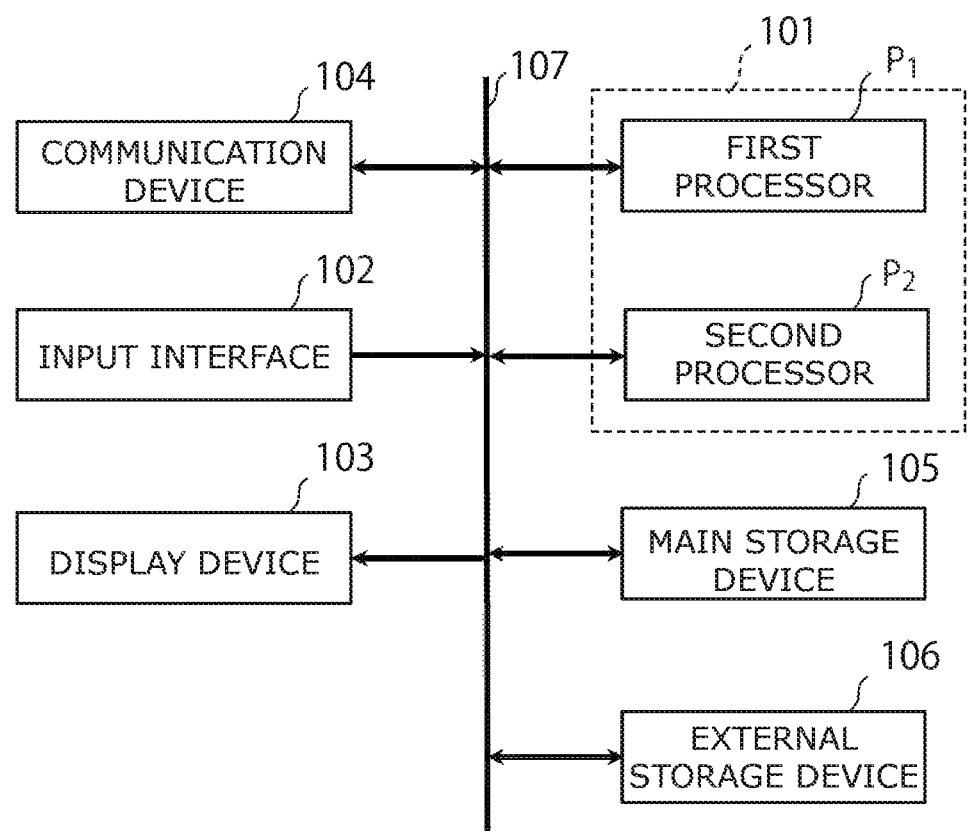
FIG. 20 is a block diagram illustrating a hardware configuration of the biological information measurement device of FIG. 18.

Next, a hardware configuration of the measurement device in accordance with the fifth embodiment is described with reference to FIG. 20. The measurement device in accordance with this embodiment includes a computer device. Output signals of the motion information sensor, the microphone, and the like are input to the computer device and subjected to a predetermined process or processes. FIG. 20 is a block diagram that illustrates the configuration of the computer device.

As illustrated in FIG. 20, the computer device includes a central processing unit (CPU) 101, an input interface 102, a display device 103, a communication device 104, a main storage device 105, and an external storage device 106, which are interconnected via a bus 107.

The CPU 101 executes a voice information processing program (hereinafter referred to as "processing program") in the main storage device 105. The above-described respective functional features are implemented by the CPU 101 executing the processing program.

In this embodiment, it is preferable that the computer device includes two CPUs 101, i.e., the first processor P1 and the second processor P2. As illustrated in FIG. 18, the first processor P1 is a CPU that configures the sleep determiner 42, the first behavior state determiner 43, and the acquisition interval controller 44 whilst the second processor P2 is a CPU that configures the voice information detector 46, the non-voice feature calculator 47, the second behavior state determiner 48, the sound feature calculator 49, and the utterance information calculator 50.

By virtue of this configuration, when the behavior state of the user is the non-utterance state, the acquisition interval controller 44 is allowed to stop the operation of the second processor P2. As a result, it is made possible to effectively reduce the power consumption by configuring all the functional features by one single CPU 101 compared with a case where processes of the individual functional features configuration are stopped.

The input interface 102 is used to input operation signals from an input device such as a keyboard, a mouse, and a touch panel into the processing device. The scheme of the input interface 102 includes, by way of example and is not limited to, USB and Ethernet. The motion information sensor, the microphone, and the like may be connected to the computer device via the input interface 102.

The display device 103 is configured to display videos based on the video signals output from the processing device. The display device is, by way of example and is not limited to, a liquid crystal display (LCD), a cathode-ray tube (CRT), and a plasma display panel (PDP). The utterance information and information such as the behavior state acquired by the computer device can be displayed by the display device 103.

The communication device 104 is a device for the computer device to perform wired or wireless communications with external devices. The utterance information and information such as the behavior state acquired by the computer device can be transmitted to the external device or devices via the communication device 104. The external devices include, by way of example and are not limited to, a smartphone and a server. The output signals of the motion information sensor, the microphone, and the like may be input to the computer device via the communication device 104.

The main storage device 105 is configured to store, when the processing, program is executed, the processing program, data necessary for execution of the processing program, data generated by the execution of the processing program, and the like. The processing program is deployed onto the main storage device 105 and thus executed. The main storage device 105 includes, by way of example and is not limited to, RAM, DRAM, and SRAM.

The external storage device 106 is configured to store the processing program, the data necessary for execution of the processing program, the data generated by the execution of the processing program, and the like. The program and the data are read out into the main storage device 105 when the processing program is executed. The external storage device 106 includes, by way of example and is not limited to, a hard disc, an optical disc, flash memory, and a magnetic tape.

It should be noted that the processing program may be installed in advance onto the computer device or stored in a storage medium such as CD-ROM. Also, the processing program uploaded to the Internet may be downloaded as required.

Figure 21:
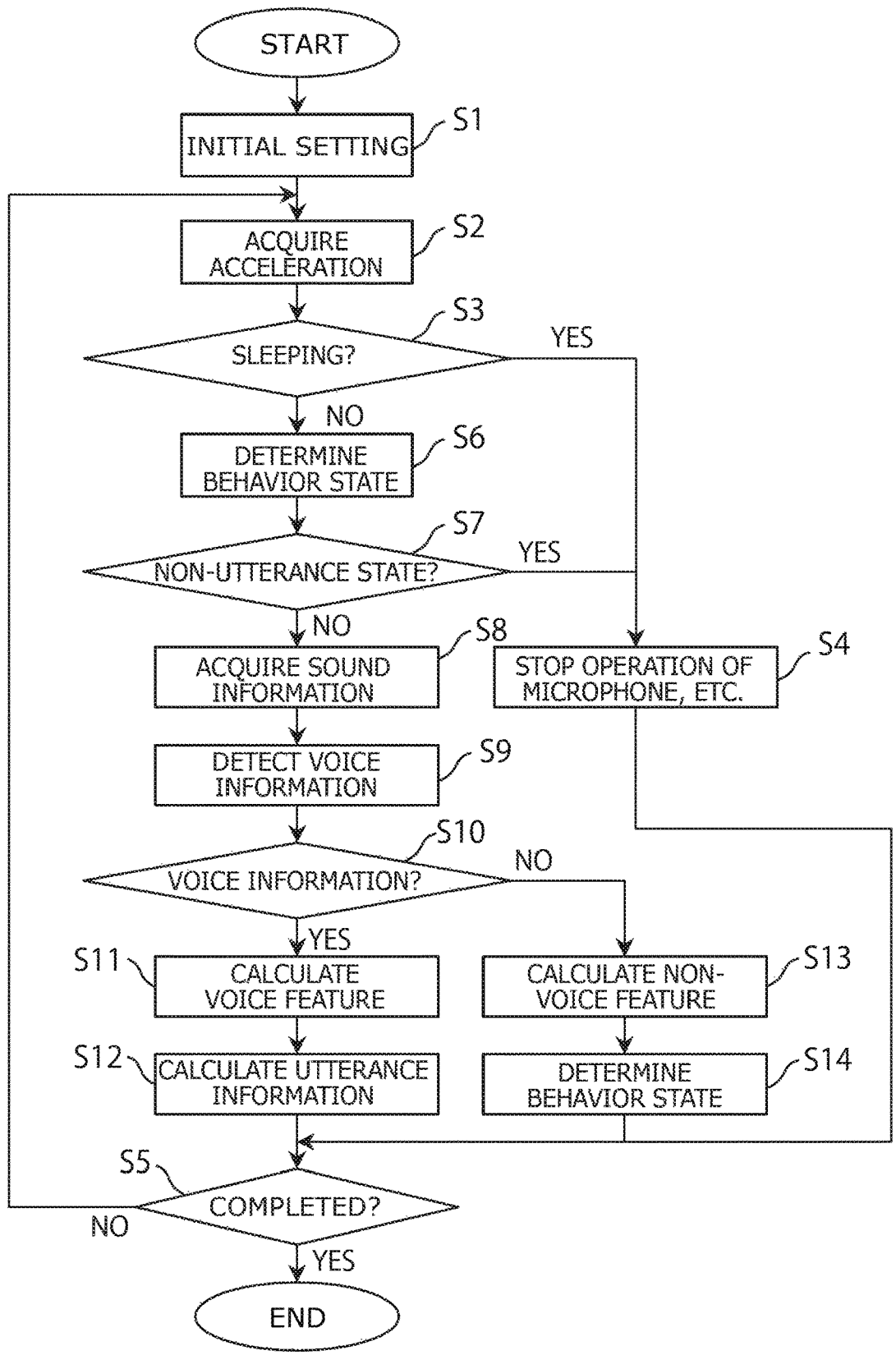
FIG. 21 is a flowchart illustrating the operation of the biological information measurement device of FIG. 18.

Next, the operation of the measurement device in accordance with this embodiment is specifically described with reference to FIG. 21. It is assumed in the following explanations that the motion information is acceleration and that the body motion amount is calculated from the acceleration as the feature. Meanwhile, as has been discussed in the foregoing, the motion information and its feature are not limited to them. FIG. 21 is a flowchart that illustrates the operation of the measurement device.

As illustrated in FIG. 21, when the processing of the sound information by the measurement device is started, then initial settings are made to the acquisition interval of the sound information and the like in the step S1. The processing of the measurement device is, for example, started at the timing at which the power supply of the measurement device is turned on or upon reception of the start signal from the user.

Next, the motion information measurer 41 acquires the acceleration of the user in the step S2. Specifically, the motion information measurer 41 calculates the acceleration of the user from the output signal of the acceleration sensor. The acceleration sensor is, by way of example and not limited to, a uniaxial, biaxial, or triaxial acceleration sensor.

In the step S3, the sleep determiner 42 calculates the body motion amount of the user from the acceleration acquired by the motion information measurer 41. The sleep determiner 42 calculates, as the body motion amount, for example, a two-axis or three-axis composite acceleration, the average value of the composite acceleration, or the number of times of the composite acceleration exceeding a particular threshold. The sleep determiner 42 determines whether or not the user is sleeping on the basis of the calculated body motion amount. The result of determination is transmitted to the acquisition interval controller 44. When the user is sleeping (YES in the step S3), the process goes to the step S4. When the user is awake (NO in the step S3), the process goes to the step S6.

When the user is sleeping, the acquisition interval controller 44 turns the microphone off in the step S4 and thereby stops the operation of the sound information acquirer 45. Also, the acquisition interval controller 44 stops the operation of the second processor P2. Specifically, the acquisition interval controller 44 stops the operation of the voice information detector 46, the non-voice feature calculator 47, the second behavior state determiner 48, the sound feature calculator 49, and the utterance information calculator 50.

After that, the measurement device determines whether or not the processing should be terminated in the step S5. The processing by the measurement device is terminated, for example, at the timing at which the power supply of the measurement device is turned off or upon reception of an end signal from the user (YES in the step S5). When the processing is not terminated (NO in the step S5), the process goes back to the step S2.

In contrast, if the user is awake, the first behavior state determiner 43 calculates the body motion amount of the user from the acceleration acquired by the motion information measurer 41 in the step S6, and determines the behavior state of the user on the basis of the body motion amount. The result of determination is transmitted to the acquisition interval controller 44.

In the step S7, the acquisition interval controller 44 determines whether or not the behavior state of the user is a non-utterance state. When the behavior state of the user is a non-utterance state (YES in the step S7), the process goes to the step S4. When behavior state of the user is not a non-utterance state (NO in the step S7), the process goes to the step S8.

In the step S8, the sound information acquirer 45 acquires the sound information at a predetermined acquisition timing. Specifically, the sound information acquirer 45 collects sounds by the microphone, subjects the output signal of the microphone to a predetermined process or processes such as AD conversion, and generates the sound information.

Next, in the step S9, the voice information detector 46 detects voice information from the sound information. When the voice information has been detected by the voice information detector 46 (YES in the step S10), the process goes to the step S11. When the voice information has not been detected (NO in the step S10), the process goes to the step S13.

When the voice information has been detected, the sound feature calculator 49 calculates the sound feature from the voice information in the step S11.

In addition, in the step S12, the utterance information calculator 50 determines the speaker from the sound feature, and calculates the utterance information such as the user's utterance time and the utterance amount as well as the utterance time and the utterance amount of a third party. The utterance information obtained in accordance with the above processing is displayed, for example, on the display device 103. After that, the process goes to the step S5.

In contrast, when the voice information has not been detected, the non-voice feature calculator 47 calculates the non-voice feature from the non-voice information in the step S13.

In addition, the second behavior state determiner 48 determines the behavior state of the user from the non-voice feature in the step S14. The behavior state of the user thus obtained is displayed, for example, on the display device 103. After that, the process goes to the step S5.

The measurement device repeats the above processing steps S1 to S14 for each acquisition interval of the sound information until the processing is completed.

As has been described in the foregoing, according to the measurement device in accordance with this embodiment, the microphone intermittently operates and the microphone does not operate when the behavior state of the user is the non-utterance state. Here, the power consumption of the measurement device is discussed.

For example, in the case of computer device (including the motion information sensor) that is capable of operating for fourteen days with a 200 mAh battery, the power consumed by the computer device is 595 µA per hour (=200 mAh/14 days×24 hours). It is supposed here that the measurement device is configured by this computer device and a microphone whose power consumption is 700 µA. If the microphone is continuously operated, the operating time of the measurement device will be 6.43 days.

In contrast, if the microphone is only intermittently operated for a ⅕ hour, the operating time of the measurement device will be 11.33 days. When the operation of the microphone is stopped while the user is sleeping and the sleeping time is 8 hours per day, then the operating time of the measurement device will be 12.10 days. When the operation of the microphone is stopped at the time of the non-utterance state during waking, the operating time of the measurement device will be further made longer than 12.10 days.

In this manner, according to this embodiment, the power consumption of the measurement device can be reduced and the operating time can be extended. By virtue of this, it is made possible to achieve downsizing of the battery and the measurement device.

Also, the measurement device in accordance with this embodiment is capable of readily continuously acquiring utterance information such as the user's utterance time, utterance amount, and the conversation time. The utterance information acquired by the measurement device can be used in mental healthcare and prevention of dementia for elderly people.

Although, the non-voice feature calculator 47 and the sound feature calculator 49 operate in a mutually exclusive manner in the above explanations, they may operate simultaneously when the sound information includes both the voice activity and the non-voice activity.

Further, the measurement device may include a stress estimator 51 configured to estimate stress of the user on the basis of the utterance information calculated by the utterance information calculator 50. The stress estimator 51 may estimate the stress of the user from the utterance information only or may estimate the stress of the user by correcting, by the utterance information, the stress estimated by autonomic nerve analysis using the number of pulses obtained from a not-shown photoelectric pulse wave sensor and a heart rate obtained from an electrocardiogram sensor.

Figure 22:
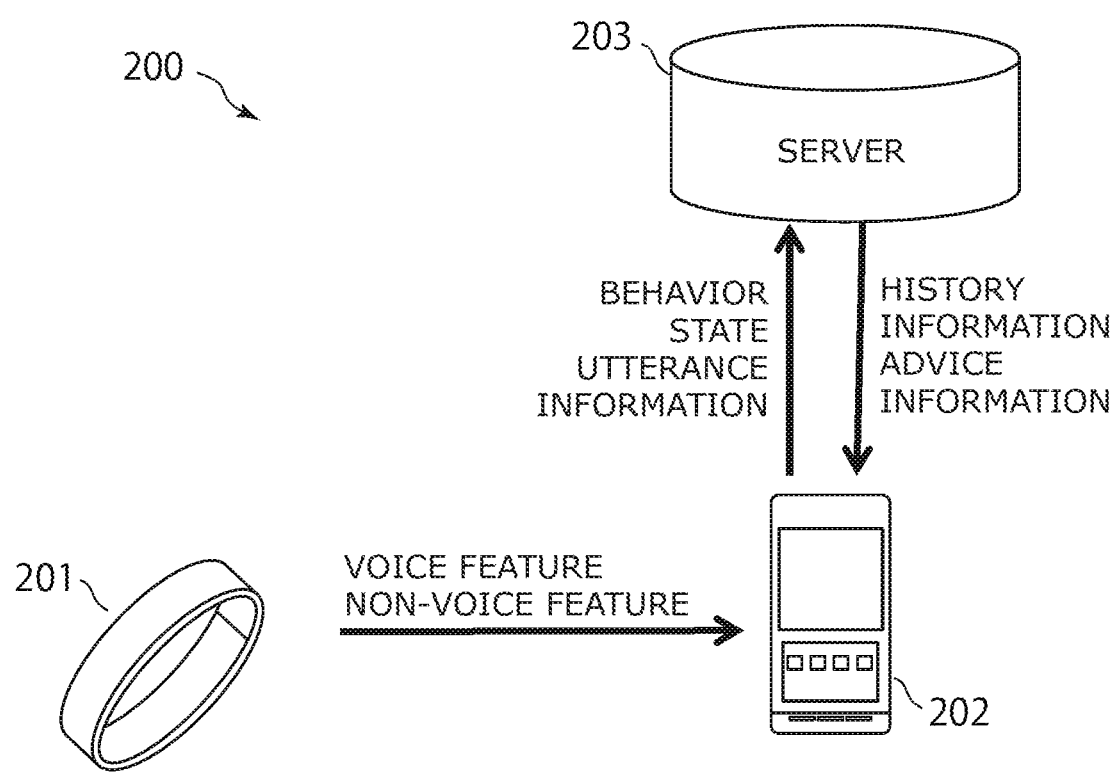
FIG. 22 is a schematic configuration diagram illustrating a biological information measurement system in accordance with the fifth embodiment.

In the above explanations, descriptions have been made based on, the case where the measurement device is configured by one single device. Meanwhile, the measurement device can be configured as a measurement system 200 constituted by multiple devices. Here, the measurement system 200 in accordance with this embodiment is described with reference to FIGS. 22 and 23. FIG. 22 is a schematic configuration diagram that illustrates an example of the measurement system 200 in accordance with this embodiment.

As illustrated in FIG. 22, the measurement system 200 includes a sensor node terminal 201, a host terminal 202, and a server 203. The sensor node terminal 201, the host terminal 202, and the server 203 are interconnected by wired or wireless connection so that communications can be performed among them.

Figure 23:
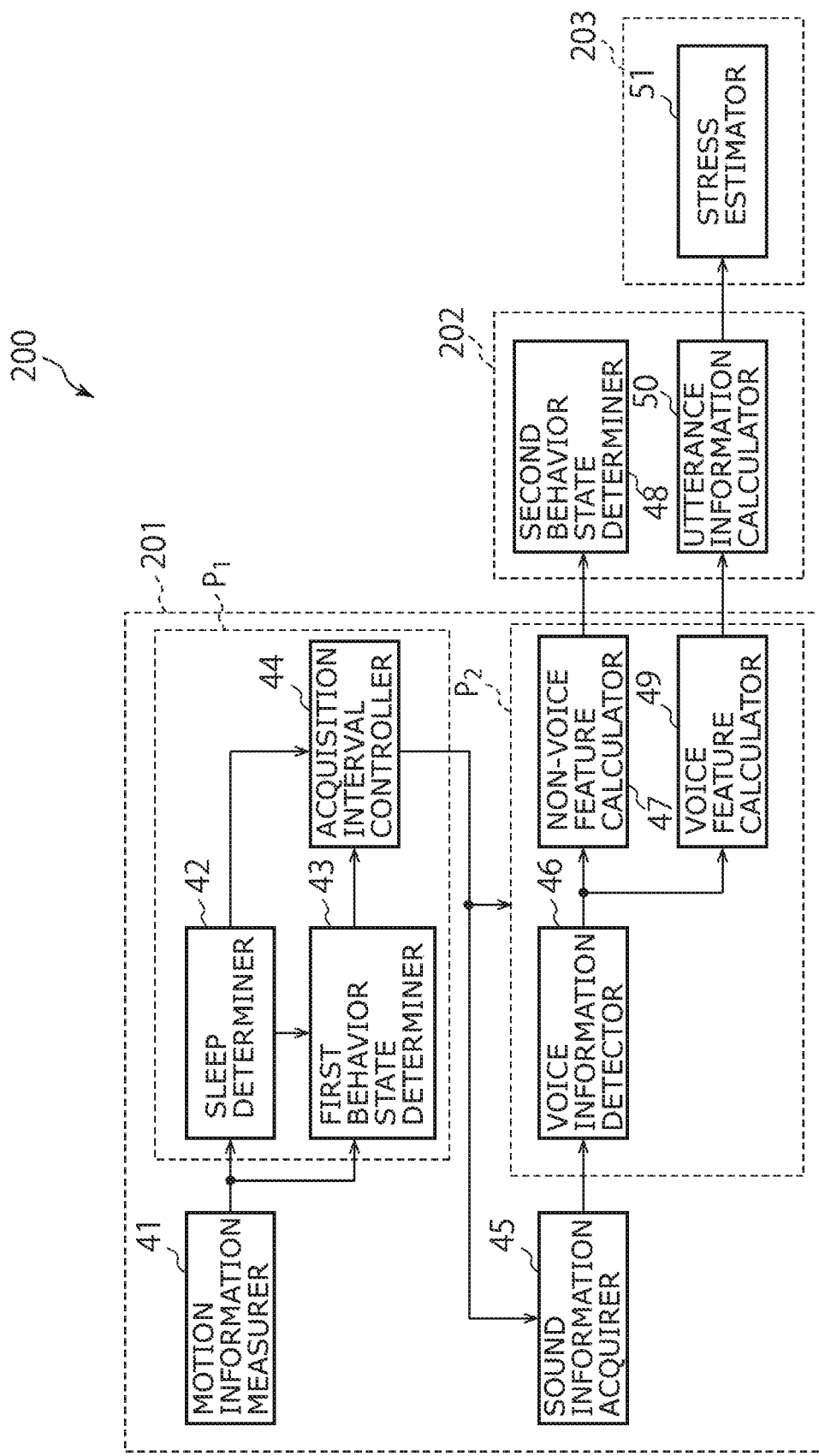
FIG. 23 is a block diagram illustrating a functional configuration of the biological information measurement system of FIG. 22.

The sensor node terminal 201 (biological information measurement device) is by way of example a wearable terminal of finger ring type, bracelet type, sticker type, or the like and configured to acquire the motion information of the user, sound information around the user, and/or other relevant information. As illustrated in FIG. 23, the sensor node terminal 201 includes the motion information measurer 41, the sleep determiner 42, the first behavior state determiner 43, the acquisition interval controller 44, the sound information acquirer 45, the sound information detector 46, the non-voice feature calculator 47, and the sound feature calculator 49. The sensor node terminal 201 transmits to the host terminal 202 a non-voice feature calculated by the non-voice feature calculator 47 and the sound feature calculated by the sound feature calculator 49.

The host terminal 202 is by way of example a smartphone, on which an application that calculates the utterance information is installed. As illustrated in FIG. 23, the host terminal 202 includes the second behavior state determiner 48 and the utterance information calculator 50. The host terminal 202 acquires the utterance information and the behavior state of the user on the basis of the voice information and the non-voice information received from the sensor node terminal 201 and transmits them to the server 203.

The server 203 is by way of example a cloud server that provides health care services. As illustrated in FIG. 23, the server 203 includes a stress estimator 51. The server 203 stores the behavior state and the utterance information received from the host terminal 202 and estimates the stress of the user from the utterance information. The server 203 transmits to the host terminal 202 pieces of information such as history information of the stored behavior state and utterance information, the estimated stress, and the advice for the user.

As has been described in the foregoing, according to the sensor node terminal 201 in accordance with this embodiment, the microphone intermittently operates and the microphone does not operate when the behavior state of the user is the non-utterance state. Accordingly, according to this embodiment, it is made possible to reduce the power consumption of the sensor node terminal 201, thereby ensuring a longer operating time. By virtue of this, it is also made possible to achieve downsizing of the battery and the sensor node terminal 201.

It should be noted that the functional features of the sensor node terminal 201, the host terminal 202, and the server 203 of the measurement system 200 in accordance with this embodiment are not limited to those of FIG. 23. For example, the voice information detector 46, the non-voice feature calculator 47, and the sound feature calculator 49 may be provided not in the sensor node terminal 201 but in the host terminal 202. Also, the stress estimator 51 may be provided not in the server 203 but in the host terminal 202. Further, the host terminal 202 may not be provided and the server 203 may include the second behavior state determiner 48 and the utterance information calculator 50.

Sixth Embodiment

Figure 24:
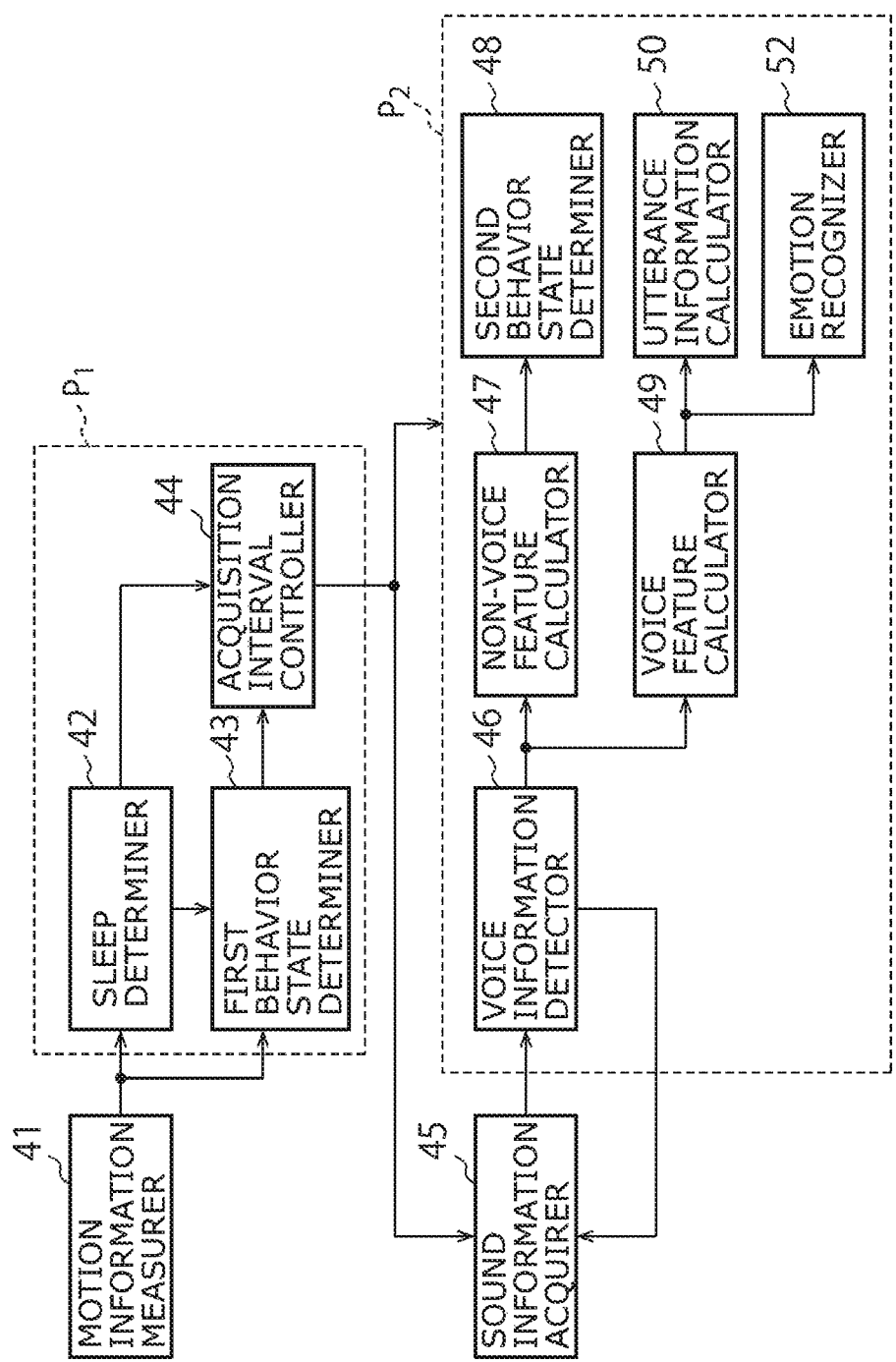
FIG. 24 is a block diagram illustrating a functional configuration of a biological information measurement device in accordance with a sixth embodiment.
Figure 25:
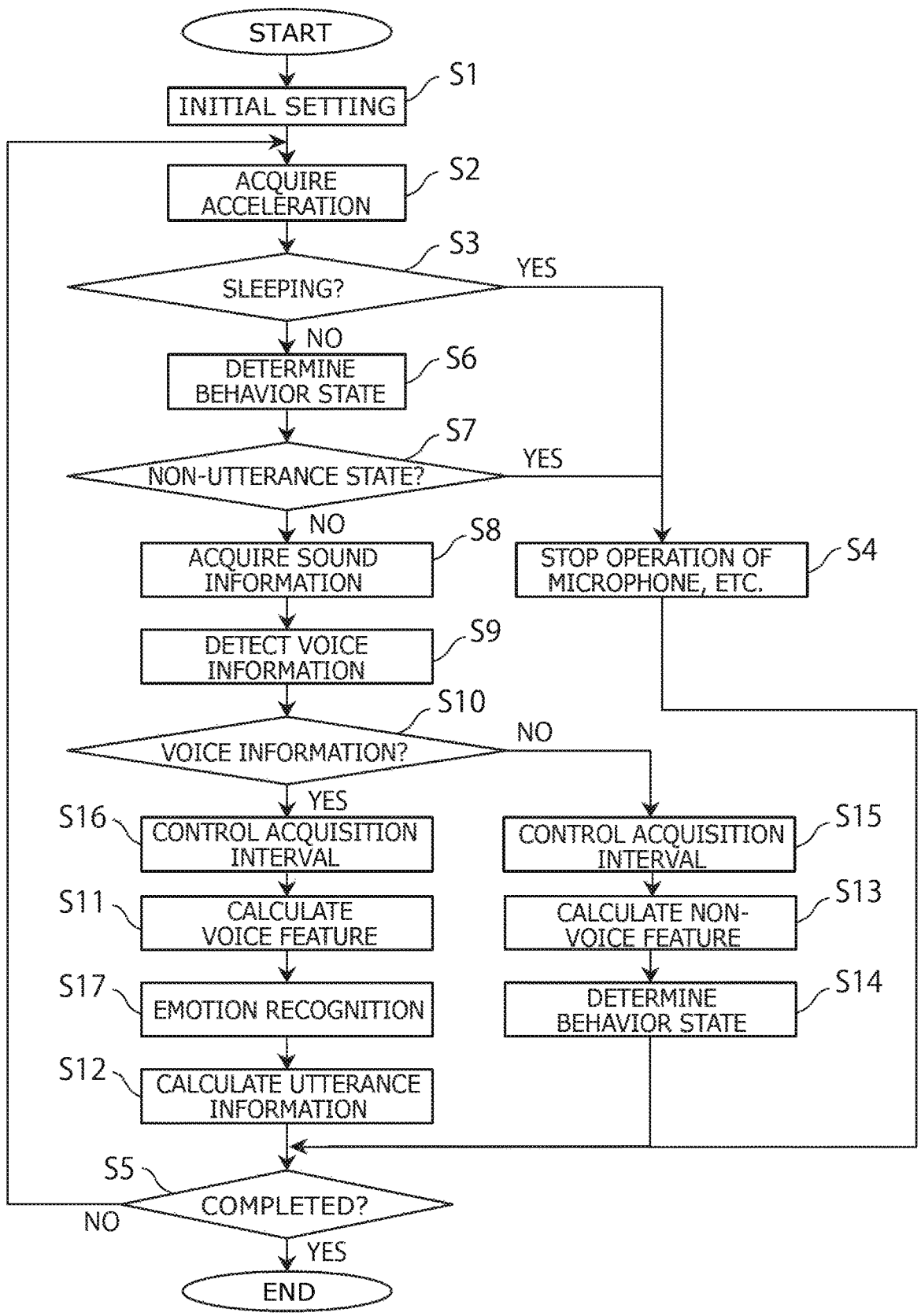
FIG. 25 is a flowchart illustrating the operation of the biological information measurement device of FIG. 24.

The measurement device in accordance with a sixth embodiment is described with reference to FIGS. 24 and 25. FIG. 24 is a block diagram that illustrates a functional configuration of the measurement device in accordance with this embodiment. As illustrated in FIG. 24, the measurement device includes the voice information detector 46 that controls the sound information acquirer 45 and further includes an emotion recognizer 52. The remaining features are the same as those in the fifth embodiment.

In this embodiment, when the voice information detector 46 has detected the voice information from the sound information, the voice information detector 46 shortens the acquisition interval of the sound information by the sound information acquirer 45 compared with a case where the voice information is not detected. By virtue of this, the voice information when the user makes an utterance can be efficiently acquired.

The emotion recognizer 52 is configured to carry out emotion recognition of the user's emotion on the basis of the sound feature for the emotion recognition calculated by the sound feature calculator 49. The emotion recognizer 52 assigns to the voice information labels such as delight, anger, sorrow, and pleasure of the user; the level of excitement; and forcefulness of the voice. For example, with regard to forcefulness of voice, "Examination Regarding Voice Forcefulness Parameter Focusing on Waveform Features" (Sugiura et al, Journal of the Acoustical Society of Japan (September 2008) or the like may be relied on. It is preferable that the emotion recognizer 52 is configured by the second processor P2.

Next, the operation of the measurement device in accordance with this embodiment is described with reference to FIG. 25. FIG. 25 is a flowchart that illustrates the operation of the measurement device in accordance with this embodiment. As illustrated in FIG. 25, the operation of the measurement device in accordance with this embodiment further includes the steps S15, S16, and S17. The remaining processing steps are the same as those in the fifth embodiment.

In this embodiment, when the voice information has been detected from the sound information (YES in the step S10), the process goes to the step S16. In the step S16, the sound information detector 6 controls the acquisition interval of the sound information by the sound information acquirer 45 such that the acquisition interval is set to the short acquisition interval for the case where the voice information is detected.

In addition, after the sound feature calculator 49 has calculated the sound feature (step S11), the emotion recognizer 52 carries out emotion recognition of the emotion of the user from the calculated sound feature in the step S17, and the process goes to the step S12.

In contrast, when the voice information has not been detected from the sound information (NO in the step S10), the process goes to the step S15. In the step S15, the sound information detector 6 controls the acquisition interval of the sound information by the sound information acquirer 45 such that the acquisition interval is set to the long acquisition interval for the case where the voice information is not detected (a case where non-voice information is detected). After that, the process goes to the step S13.

As has been described in the foregoing, when the voice information has been detected, the measurement device in accordance with this embodiment shortens the acquisition interval of the sound information. By virtue of this, the voice information can be efficiently acquired. Also, recognition of the emotion of the user can be carried out by the emotion recognizer 52.

It should be noted in this embodiment that the processing of the step S16 can be performed at any appropriate timing anywhere in the section from the step S10 to the step S5 when the voice information has been detected from the sound information. Also, the processing of the step S17 can be performed at any appropriate timing anywhere in the section from the step S11 to the step S5.

Further, the measurement system 200 in accordance with this embodiment may include the host terminal 202 that includes the emotion recognizer 52 or the server 203 that includes the emotion recognizer.

Seventh Embodiment

Figure 26:
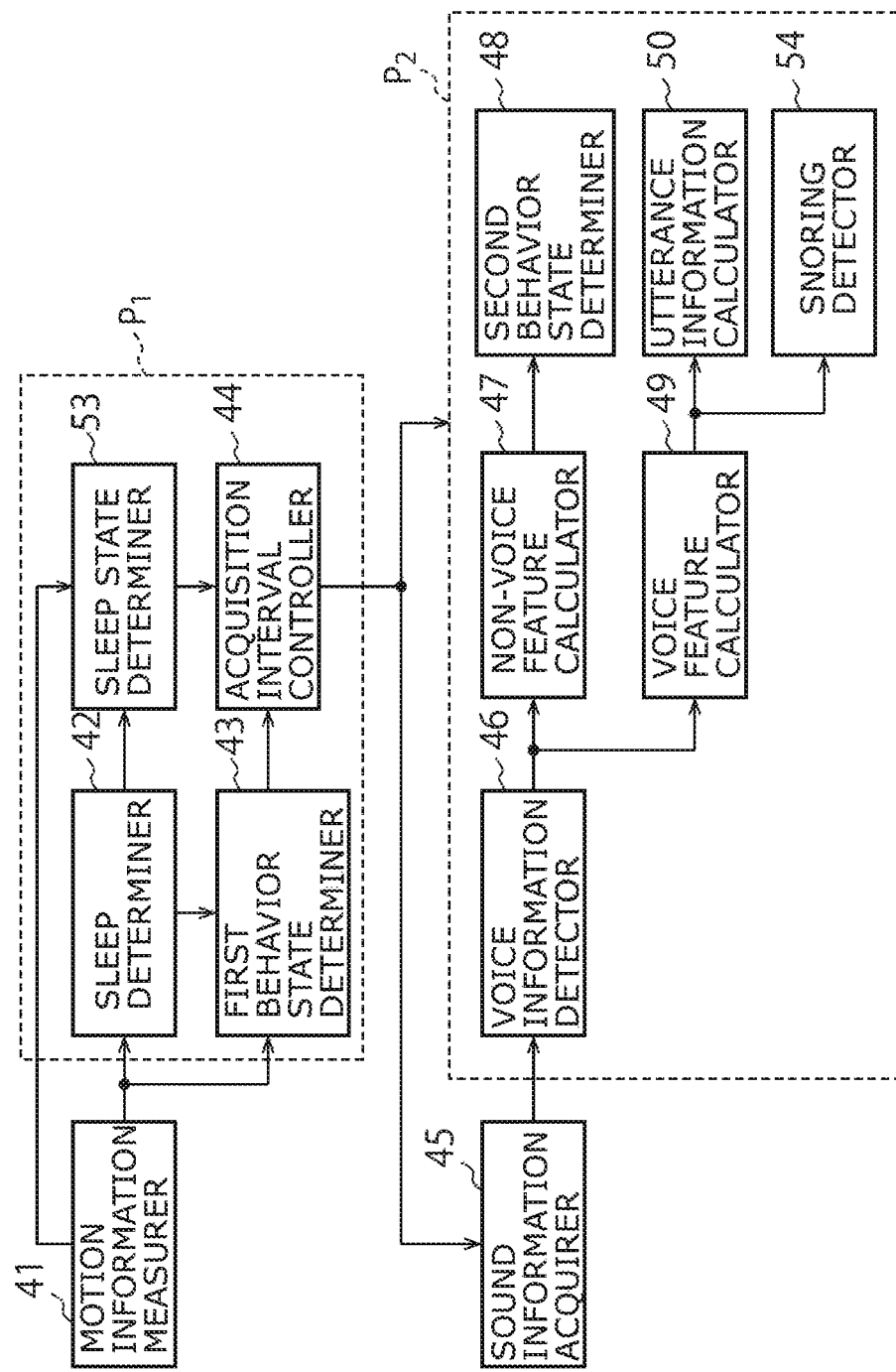
FIG. 26 is a block diagram illustrating a functional configuration of a biological information measurement device in accordance with a seventh embodiment.

The measurement device in accordance with the seventh embodiment is described with reference to FIG. 26. FIG. 26 is a block diagram that illustrates the functional configuration of the measurement device in accordance with this embodiment. As illustrated in FIG. 26, the measurement device further includes a sleep state determiner 53 and a snoring detector 54. The remaining features are the same as those in the fifth embodiment.

The sleep state determiner 53 is configured to determine the depth of the user's sleep on the basis of the motion information of the user acquired by the motion information measurer 41. The sleep state determiner 53 by way of example calculates the feature such as the body motion amount of the user from the motion information and can determine whether the sleep of the user is shallow or deep on the basis of the calculated feature.

The sleep state determiner 53 acquires the result of determination of the sleep determiner 42 and determines the depth of the user's sleep only when the user is sleeping. Accordingly, the sleep state determiner 53 does not operate when it has been determined by the sleep determiner 42 that the user is awake. It is preferable that the sleep state determiner 53 is configured by the first processor P1.

In the fifth embodiment, the acquisition interval controller 44 stops the sound information acquirer 45 and the second processor P2 when the user is sleeping. Meanwhile, in this embodiment, the acquisition interval controller 44 causes the sound information acquirer 45, the voice information detector 46, the sound feature calculator 49, and the snoring detector 54 to operate when the sleep state determiner 53 has determined that the user's sleep is shallow though the user is sleeping.

The snoring detector 54 is configured to detect snoring of the user on the basis of the sound feature for the sound feature calculator 49 to detect the calculated snoring. As such a sound feature, formant frequency, envelope, peak frequency, and the like may be mentioned. It is preferable that the snoring detector 54 is configured by the second processor P2.

Figure 27:
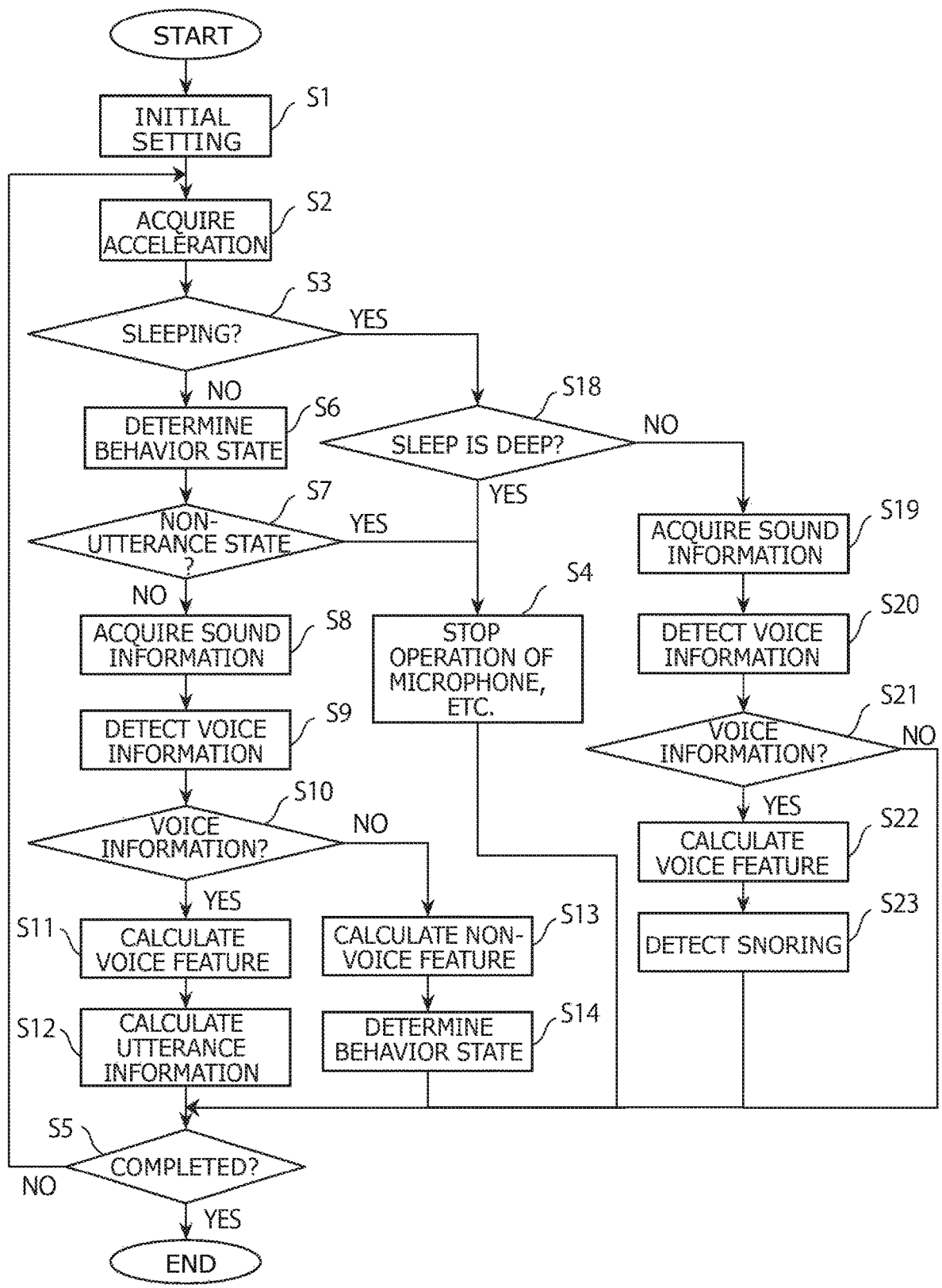
FIG. 27 is a flowchart illustrating the operation of the biological information measurement device of FIG. 26.

Next, the operation of the measurement device in accordance with this embodiment is described with reference to FIG. 27. FIG. 27 is a flowchart that illustrates the operation of the measurement device in accordance with this embodiment. As illustrated in FIG. 27, the operation of the processing device in accordance with this embodiment further includes the steps S18 to S23. The remaining processing steps are the same as those in the fifth embodiment.

In this embodiment, when the user is sleeping (YES in the step S3), the process goes to the step S18. In the step S18, the sleep state determiner 53 determines the depth of the sleep of the user. When the sleep of the user is deep (YES in the step S18), the process goes to the step S4. When the sleep of the user is shallow (NO in the step S18), the process goes to the step S19.

In the step S19, the sound information acquirer 45 acquires the sound information at a predetermined acquisition timing. Specifically, the sound information acquirer 45 collects sounds by the microphone, subjects the output signal of the microphone to a predetermined process or processes such as AD conversion, and generates the sound information.

Next, in the step S20, the voice information detector 46 detects voice information from the sound information. When the voice information has not been detected by the voice information detector 46 (NO in the step S21), the process goes to the step S5. When the voice information has been detected (YES in the step S21), the process goes to the step S22.

When the voice information has been detected, the sound feature calculator 49 calculates the sound feature for detecting snoring from the voice information in the step S22.

In addition, the snoring detector 54 detects snoring from the sound feature in the step S23. After that, the process goes to the step S5.

As has been described in the foregoing, the measurement device in accordance with this embodiment detects the snoring of the user from the sound feature when the user's sleep is shallow. A patient of sleep apnea syndrome (SAS) snores using his/her vocal cord. As a result, diagnosis of sleep apnea syndrome can be performed by using the measurement device in accordance with this embodiment to detect snoring of the user and collect the sounds of the snoring.

It should be noted that the measurement system 200 in accordance with this embodiment may include the host terminal 202 that includes the snoring detector 54 or the server 203 that includes the snoring detector 54.

The present invention is not limited to the above described embodiments as they are, and constituent elements can be substantiated with deformation within a range not deviating from the gist thereof in a practical phase. Various inventions can be formed by appropriate combinations of the plurality of constituent elements disclosed in the above described embodiments. For example, some constituent elements can be deleted from all the constituent elements shown in the embodiments, and the elements across the different embodiments can be appropriately combined.

The invention claimed is:

1. A biological information measurement device comprising:
   a sound information acquirer configured to perform intermittent acquisition of sound information around a user; and
   a voice information detector configured to detect voice information from the sound information,
   wherein the voice information detector shortens an acquisition interval in intermittent acquisition by the sound information acquirer in response to the voice information being detected such that the length of the acquisition interval becomes shorter than that of an acquisition interval in a case where the voice information is not detected.

2. The device according to claim 1, comprising:
   a motion information measurer configured to acquire motion information of the user;
   a sleep determiner configured to determine whether or not the user is sleeping on the basis of the motion information;
   a first behavior state determiner configured to determine a behavior state of the user on the basis of the motion information when the user is awake; and
   a controller configured to select one intermittent acquisition from multiple intermittent acquisitions having different measurement intervals on the basis of results of determination of the sleep determiner and the first behavior state determiner and control the sound information acquirer.

3. A biological information measurement device comprising:
   a sound information acquirer configured to perform intermittent acquisition of sound information around a user;
   a motion information measurer configured to acquire motion information of the user;
   a sleep determiner configured to determine whether or not the user is sleeping on the basis of the motion information;
   a voice information detector configured to detect voice information from the sound information;
   a sound feature calculator configured to calculate a feature of the voice information included in the sound information; and
   a non-voice feature calculator configured to calculate a feature of non-voice information included in the sound information,
   a controller configured to stop operation of at least any one of the voice information detector, the sound feature calculator, and the non-voice feature calculator when the user is sleeping.

4. The device according to claim 3, comprising:
   a first behavior state determiner configured to determine a behavior state of the user on the basis of the motion information when the user is awake; and
   wherein the controller configured to select one intermittent acquisition from multiple intermittent acquisitions having different measurement intervals on the basis of results of determination of the sleep determiner and the first behavior state determiner and control the sound information acquirer.

* * * * *